United States Patent
Lord

(10) Patent No.: US 11,571,692 B2
(45) Date of Patent: Feb. 7, 2023

(54) ATTACHMENT METHOD FOR MICROFLUIDIC DEVICE

(71) Applicant: PhysioLogic Devices, Inc., Alpine, CA (US)

(72) Inventor: Peter C. Lord, Alpine, CA (US)

(73) Assignee: PhysioLogic Devices, Inc., Alpine, CA (US)

(*) Notice: Subject to any disclaimer, the term of this patent is extended or adjusted under 35 U.S.C. 154(b) by 370 days.

(21) Appl. No.: 16/017,694

(22) Filed: Jun. 25, 2018

(65) Prior Publication Data
US 2019/0030529 A1    Jan. 31, 2019

Related U.S. Application Data

(60) Provisional application No. 62/524,373, filed on Jun. 23, 2017.

(51) Int. Cl.
*B01L 3/00* (2006.01)
*B81C 3/00* (2006.01)
(Continued)

(52) U.S. Cl.
CPC ... *B01L 3/502707* (2013.01); *A61M 5/14276* (2013.01); *B01L 3/502715* (2013.01); *B81C 3/001* (2013.01); *F04B 43/043* (2013.01); *A61M 2205/0244* (2013.01); *B01L 2400/0487* (2013.01); *B81C 2201/0181* (2013.01)

(58) Field of Classification Search
CPC ......... B01L 3/502707; B01L 3/502715; B01L 2400/0487; F04B 43/043; A61M 5/14276; A61M 2205/0244; B81C 3/001; B81C 2201/0181
See application file for complete search history.

(56) References Cited

U.S. PATENT DOCUMENTS 5,899,752 A * 5/1999 Hey .................. H01L 21/02046
                                              438/791
6,699,394 B2 * 3/2004 Tai ........................ F04B 43/043
                                              216/2
(Continued)

FOREIGN PATENT DOCUMENTS

CN         103589983 A  *  2/2014
WO    WO-2006110177 A2  * 10/2006 ............ F04B 19/006

OTHER PUBLICATIONS

Vogel et al (Electroplating—A Comparison of Electroless and Electrolytic Nickel, Products Finishing, 4 pages, 2007) (Year: 2007).*

(Continued)

*Primary Examiner* — Benjamin R Whatley
*Assistant Examiner* — Jean Caraballo-Leon

(57) ABSTRACT

A microfluidic device includes a silicon device and a metallic component. The silicon device and the metallic component are attached by preparing a surface of a silicon device to be solderable, preparing a corresponding surface of a metallic component to be solderable, and soldering the prepared surface of the silicon device to the corresponding prepared surface of the metallic component with a solder of a pre-defined composition and thickness to accommodate strain due to co-efficient of thermal expansion (CTE) mismatch between the silicon device and the metallic component.

20 Claims, 35 Drawing Sheets

(51) Int. Cl.
  *F04B 43/04* (2006.01)
  *A61M 5/142* (2006.01)

(56) References Cited

U.S. PATENT DOCUMENTS

2007/0105341 A1* 5/2007 Sosnowchik .......... B23K 1/203
  438/455
2014/0069214 A1* 3/2014 Kruckow ................ B01L 9/527
  73/865.8
2015/0045234 A1* 2/2015 Stone ..................... B01L 3/527
  506/2

OTHER PUBLICATIONS

Siegel et al (Microsolidics: fabrication of Three-Dimensional Metallic Microstructures in Poly(dimethylsiloxane), Advanced Materials, 2007, pp. 727-733, see attached document) (Year: 2007).*
Mackie (Understanding Gold on Nickel, Indium Corporation Blow, 2009, 4 pages, see attached document) (Year: 2009).*
Perez (Physical Vapor Deposition—Sputtering vs Electron Beam Evaporation, Abrisa Technologies, 2012, 2 pages, see attached document) (Year: 2012).*
Lee (Chapter 10—Diffusion bonding of metal alloys in aerospace and other applications, Welding and Joining of Aerospace Materials, Woodhead Publishing Series in Welding and Other Joining Technologies, 2012, pp. 320-344) (Year: 2012).*
Lee et al (Fluxless Tin and Silver-Indium Bonding Processes for Silicon onto Aluminum, Journal of Electronic Materials, 2014, vol. 43, pp. 9-15, see attached document) (Year: 2014).*
The Indium Corporation (The Versatile Preform, The Indium Corporation Youtube Channel, 2016 (Year: 2016).*
The Indium Corporation II (Solder Preforms Product Data Sheet, The Indium Corporation, 2017 (Year: 2017).*
Bal Seal Engineering (Electroless nickel plating: A general description of electroless nickel plating and its effect on Bal Seal® spring-energized seal performance in reciprocating and rotary service, Technical Response, 2016 (Year: 2016).*
Thermofisher (How Gold Plating is done, Step by Step, Thermofisher, 2015 (Year: 2015).*
Products Finishing (Who Really Cares About the Surface Preparation Requirements for the Successful Application of Electroless Nickel?, Electroplating, 1999 (Year: 1999).*
Wu et al. (Fluxless Bonding Processes Using Silver-Indium System for High Temperature Electronics and Silver Flip-Chip Interconnect Technology, Thesis/Dissertation, UC Irvine Electronic Theses and Dissertations, 2015 (Year: 2015).*
Wang et al. (Silver Microstructure Control for Fluxless Bonding Success Using Ag—In System, IEEE, 2010, vol. 33, Issue 2, pp. 462-469 (Year: 2010).*

* cited by examiner

ATTACHMENT METHOD FOR MICROFLUIDIC DEVICE

CROSS-REFERENCE TO RELATED APPLICATIONS

This application claims the benefit of U.S. Provisional Patent Application No. 62/524,373, filed on Jun. 23, 2017, the entire disclosure of which is hereby incorporated herein by reference.

TECHNICAL FIELD

The present invention relates generally to methods for attachment of MEMS pumps and other microfluidic components in implantable medical devices. In particular, methods are disclosed for attaching various microfluidics devices made from silicon, ceramic or glass to metallic structures made from titanium, stainless steel, cobalt alloys, or other metals used in the construction of such devices.

BACKGROUND OF THE INVENTION

Using a silicon MEMS micro-pump in an implantable device requires permanently connecting a silicon surface of a piezoelectric transducer to a metal manifold, such as a titanium manifold. This involves joining two materials, silicon and titanium, that do not solder to each other, or to known solders or braze materials, either. This is because these materials do not adhere to common soldering and brazing materials, and if they did, there would be large mismatch in the co-efficient of thermal expansion (CTE) that would put an unreasonable stress on the joint—causing it to be weak or to fracture. In implantable devices, fractures are intolerable, inasmuch as the joint to a medical device must be hermetic to prevent water diffusion into the device's sensitive electronics portion. It must also reliably seal the inlet from the outlet so that there is no possibility of fluid from the inlet side passing directly to the outlet by bypassing the micropump. It is noted that it is cost effective to design MEMS micropumps with a minimum number of silicon layers, with a base layer incorporating an inlet opening and an outlet opening. The inlet and the outlet must be sealed securely to the corresponding conduits on the titanium medical device.

Therefore, what is needed in the art are techniques to hermetically bond silicon surfaces of MEMS micropumps to metallic (e.g., titanium) manifolds in MEMS pumps, so as to facilitate their use in implantable devices.

SUMMARY OF THE INVENTION

Methods for joining a MEMS chip to a titanium manifold, and related systems are presented. In embodiments, the joining of a silicon part to a titanium part is such that the parts do not break apart due to a co-efficient of thermal expansion (CTE) mismatch. In embodiments, silicon and titanium may be soldered together with a soft solder joint using indium silver, where the temperature excursion of approximately 120° F. between the solder solidus and the use temperature limits the strain between the two surfaces. Because silicon and titanium cannot be directly soldered together, in embodiments both surfaces must first be prepared. The silicon micropump surface may be treated with hydrofluoric acid to remove its silicon oxide coating, and then Ti—W, Nickel, and gold layers successively sputtered onto it. The manifold may be ground flat, and plated with electroless nickel. The nickel plated manifold may then be baked, so as to create a transition from pure Ti to Ni—Ti alloy to pure Ni at the surface of the manifold. To protect the upper Ni surface, a layer of gold may be added. Following these preparations, the two surfaces may be soldered in forming gas.

BRIEF DESCRIPTION OF THE DRAWINGS

FIG. 24 depicts the two components or subassemblies of FIG. 23 now fully attached, the process complete;

DETAILED DESCRIPTION OF THE INVENTION

Figure 1:
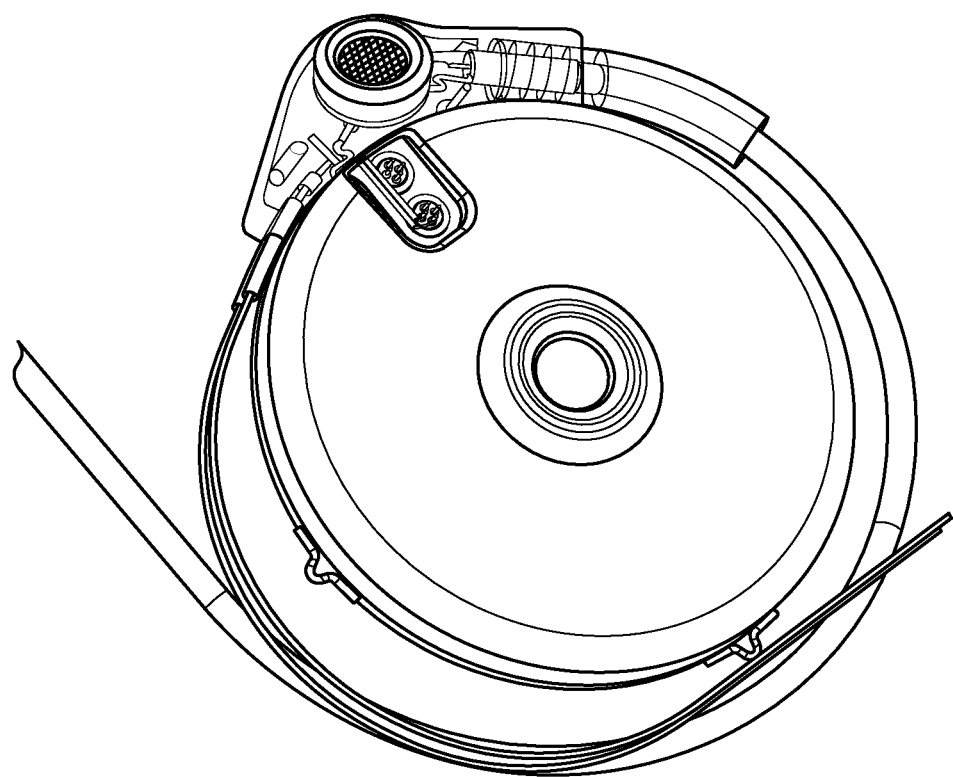
FIG. 1 depicts a top view of an exemplary implantable device with a MEMS pump, using an example attachment method in accordance with various embodiments.

The following detailed description refers to the accompanying drawings. The same reference numbers may be used in different drawings to identify the same or similar elements. In the following description, for purposes of explanation and not limitation, specific details are set forth such as particular structures, architectures, interfaces, techniques, etc., in order to provide a thorough understanding of the various aspects of various embodiments. However, it will be apparent to those skilled in the art having the benefit of the present disclosure that the various aspects of the various embodiments may be practiced in other examples that depart from these specific details. In certain instances, descriptions of well-known devices, circuits, and methods are omitted so as not to obscure the description of the various embodiments with unnecessary detail.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed or described operations may be omitted in additional embodiments.

The description may use the phrases "in an embodiment," or "in embodiments," which may each refer to one or more of the same or different embodiments. Furthermore, the terms "comprising," "including," "having," and the like, as used with respect to embodiments of the present disclosure, are synonymous.

As used herein, including in the claims, the term "circuitry" may refer to, be part of, or include an Application Specific Integrated Circuit (ASIC), an electronic circuit, a processor (shared, dedicated, or group), and/or memory (shared, dedicated, or group) that execute one or more software or firmware programs, a combinational logic circuit, and/or other suitable hardware components that provide the described functionality. In some embodiments, the circuitry may be implemented in, or functions associated with the circuitry may be implemented by, one or more software or firmware modules. In some embodiments, circuitry may include logic, at least partially operable in hardware.

The present invention relates generally to methods for attachment of MEMS pumps and other microfluidic components in implantable medical devices. In particular, methods are disclosed for attaching various microfluidics devices made from silicon, ceramic or glass to metallic structures made from titanium, stainless steel, cobalt alloys, or other metals used in the construction of such devices. The methods presented may be used in the construction of, for example, implantable devices that dispense insulin, therapeutics or other chemicals, of various types. Medical devices of this type may also pump body fluids into a chamber for measurement of various analytes including glucose or insulin. They may also transport body fluids for other purposes such as pressure equalization for hydrocephalus. They may also be used to pump a working fluid. For example, for a corrosive chemotherapeutic agent, one might pump silicone oil into a bladder within a medication reservoir. This would force the chemotherapeutic agent out of the medication reservoir without corroding the pump. One type of such implantable devices utilizes MEMS pumps to dispense the insulin. In particular, the present invention presents a novel method for attaching a silicon MEMS pump to a titanium reservoir.

Embodiments disclosed herein may be useful for attaching microfluidics devices made from silicon, ceramic or glass, to metallic structures made from titanium, stainless steel, cobalt alloys, or other metals, used in the construction of a microfluidics device.

In embodiments, possible device applications may include a micropump, a pressure sensor, a flow sensor, thermal dilution, Coriolis, a pressure drop across a restriction, a capillary flow restrictor, an optical measurement device, an electrochemical measurement device, a flow regulator, a filter, an air vent, or a pressure reference conduit for pressure operated valve or a regulator, for some non-limiting examples.

In embodiments, a method for joining a MEMS chip to a titanium manifold, and a system including such a joint may be provided. The system and method may be based on a technique for joining a silicon part to a titanium part, where, unlike conventional attempts, the silicon and titanium components do not break apart due to a thermal expansion coefficient (CTE) mismatch. In embodiments, silicon and titanium may be soldered together using an indium silver solder. Indium silver is soft, and thus can absorb the strain resulting from the thermal expansion co-efficient mismatch. Moreover, the low melting point of the indium-silver solder limits the CTE strain by limiting the temperature excursion from solidus to room temperature. Because silicon and titanium cannot be directly soldered together, in embodiments both surfaces may first be prepared for soldering. Beginning with the MEMS micropump device, the silicon may be treated with hydrofluoric acid to remove its silicon oxide coating and to optimize the adhesion of the sputtered layers. Then, immediately before the silicon oxide layer reforms, the silicon surface may be sputtered with Titanium Tungsten Alloy (TiW), Nickel, and Gold, in that order. The TiW may act as an adhesion promoter to the silicon, the nickel as the substrate for soldering to, and the gold may prevent oxidation of the nickel surface. It is noted that the gold may dissolve away during the soldering process. The opposing surface on a metallic manifold (e.g., titanium) may be plated with electroless nickel, which by itself does not adhere strongly to titanium. However, when the nickel is baked, for example at 400 degrees Celsius, it may alloy with the titanium and become strongly adhered. Following that, the nickel surface may be cleaned with ammonium hydroxide and sputtered with a second layer of nickel. The second nickel coating may then be immediately sputtered with gold to prevent oxidation of the nickel surface. After these preparations, the two surfaces may be soldered in forming gas using an indium silver solder.

FIGS. 1-17 illustrate a MEMS pump provided in an exemplary implantable device, here the PhysioLogic ThinPump™, an implantable infusion pump dispensing insulin. The device has a reservoir filled with medication, and a MEMS micropump that is joined to the reservoir so that it can draw insulin out of the reservoir and pump the medication into the body. These connections must be hermetic to a leak rate of $10^9$ cc/sec of helium to prevent diffusion of water and a gradual accumulation of moisture that will lead to corrosion, dendrite formation and short circuits on the microelectronics assembly. As a general rule this means that the joining process cannot be polymer based. A hermetic seal of this type generally requires a metallurgical joint or a glass to metal seal.

As noted, FIGS. 1-17 (and FIG. 6 in particular) illustrate various parts of an exemplary MEMS pump. In conjunction with these figures, a system and method are next described for joining the MEMS chip to a titanium manifold. At the highest level it is noted that there are two design constraints for such a MEMS pump. First, the separation between inlet and outlet must be absolute. This is because if it were not, then leakage from the inlet to the outlet would bypass the pump and its valving; this would create a situation where if a clinician were to fill the pump and leave it in a positive pressure condition, flow through this leak would drive unrequested medication forward into a patient. It is here noted that the consequences of free flow of this type can be potentially lethal. So, in embodiments, a redundant seal may be provided using O-rings. It is here noted that a compressed elastomeric O-ring creates a reliable fluidics seal because of the compression of the rubber seals in spite of minor surface imperfections. Alternatively a pressure sensitive adhesive (as illustrated in FIGS. 17G and 17H) can also work in this application because it too can also seal in spite of minor surface imperfections. An additional advantage to using a pressure sensitive adhesive is that by separating the inlet seal from the outlet seal, the assembly can be verified for inlet and outlet sealing using a helium leak test. However, the O-ring seal has the advantage that it can be used in locations where there is no opportunity for a visual verification of a seal. The O-ring seal can also seal reliably in spite of a minimal distance between the inlet and the outlet. In fact, two O-rings can be fit in a spacing of 0.028 inches between inlet and outlet, as shown for example, in FIG. 10. Thus, in the depicted embodiment of FIG. 10, a redundant rubber seal is used.

As a second MEMS pump design constraint, it is also necessary to hermetically seal the entire pump and manifold assembly fluid path away from any nearby compartment containing microelectronics. This requires a metallurgical joint to achieve the required level of hermeticity. Even diffusion through a rubber gasket is absolutely not acceptable—water vapor will likely pass through a rubber gasket and will then corrode the electrically active traces and components on the printed circuit boards, leading to device failure. So, to address both issues, in embodiments a MEMS pump may have both a mechanical attachment in the form of a metallurgic joint, and a 2× redundant rubber seal. Various embodiments described herein have both such a seal as well as a metallurgical joint.

Figure 2:
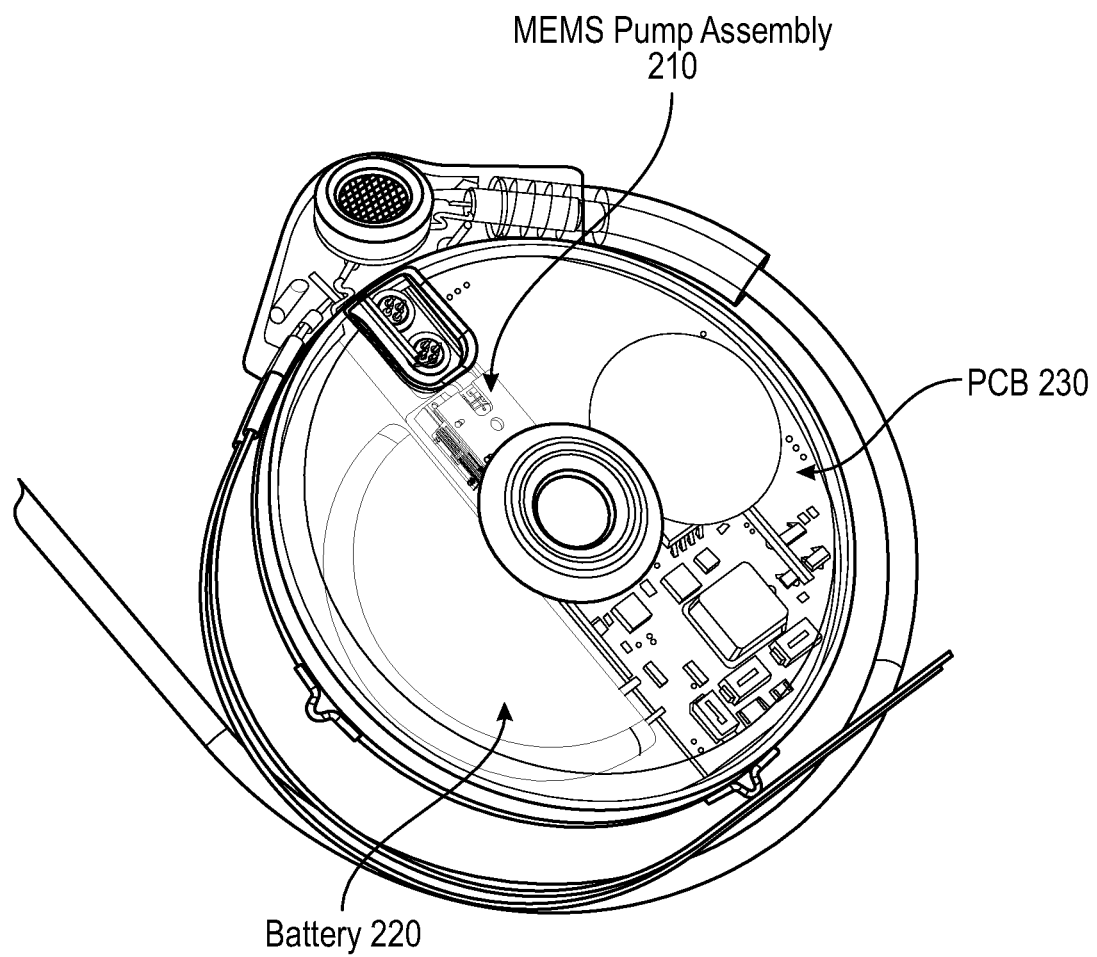
FIG. 2 shows the exemplary implantable device of FIG. 1 with a transparent cover to illustrate the interior components, and an arrow pointing to an exemplary MEMS pump assembly.
Figure 3:
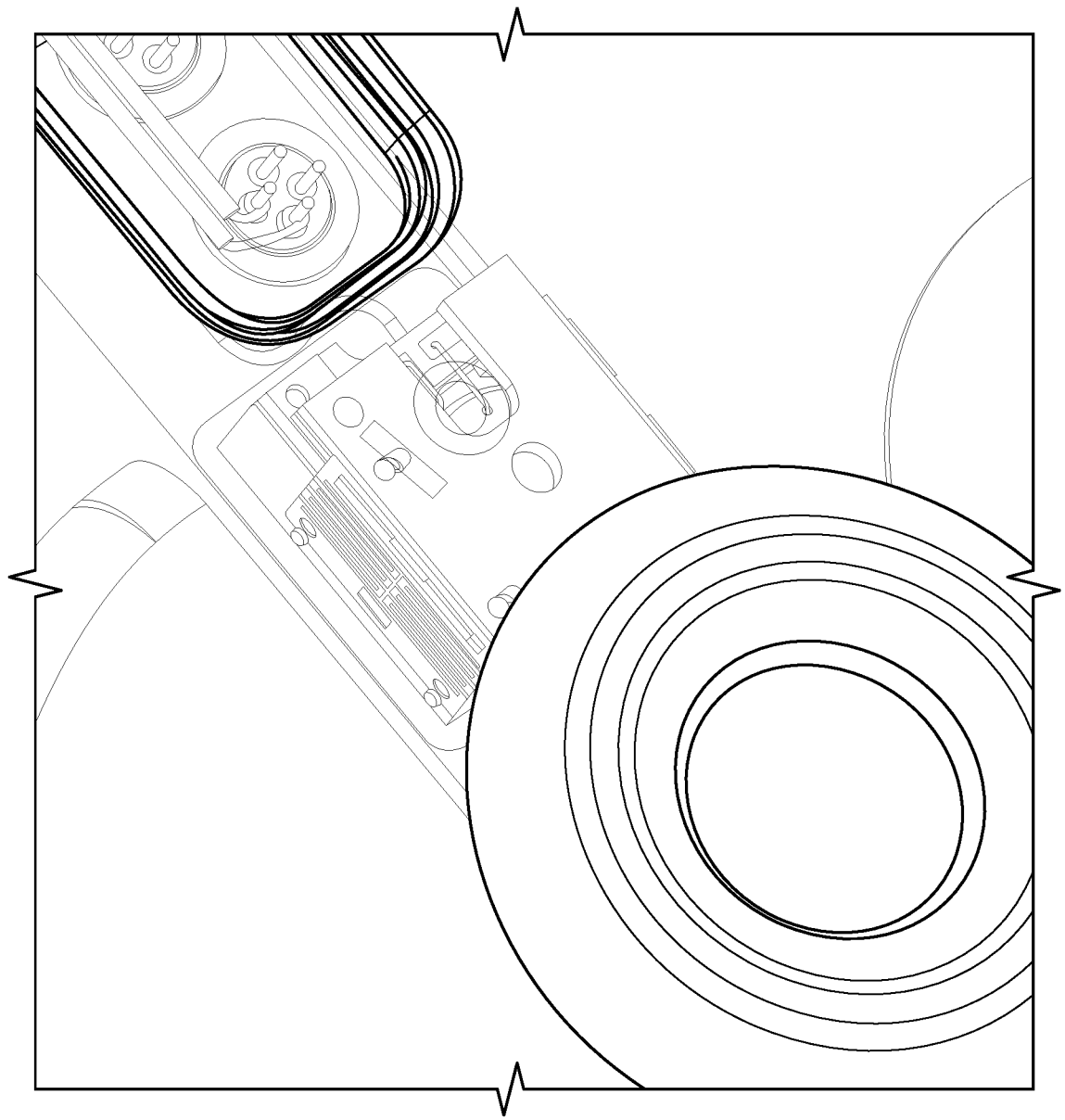
FIG. 3 depicts the MEMS pump assembly as provided in the example device in a magnified view.
Figure 4:
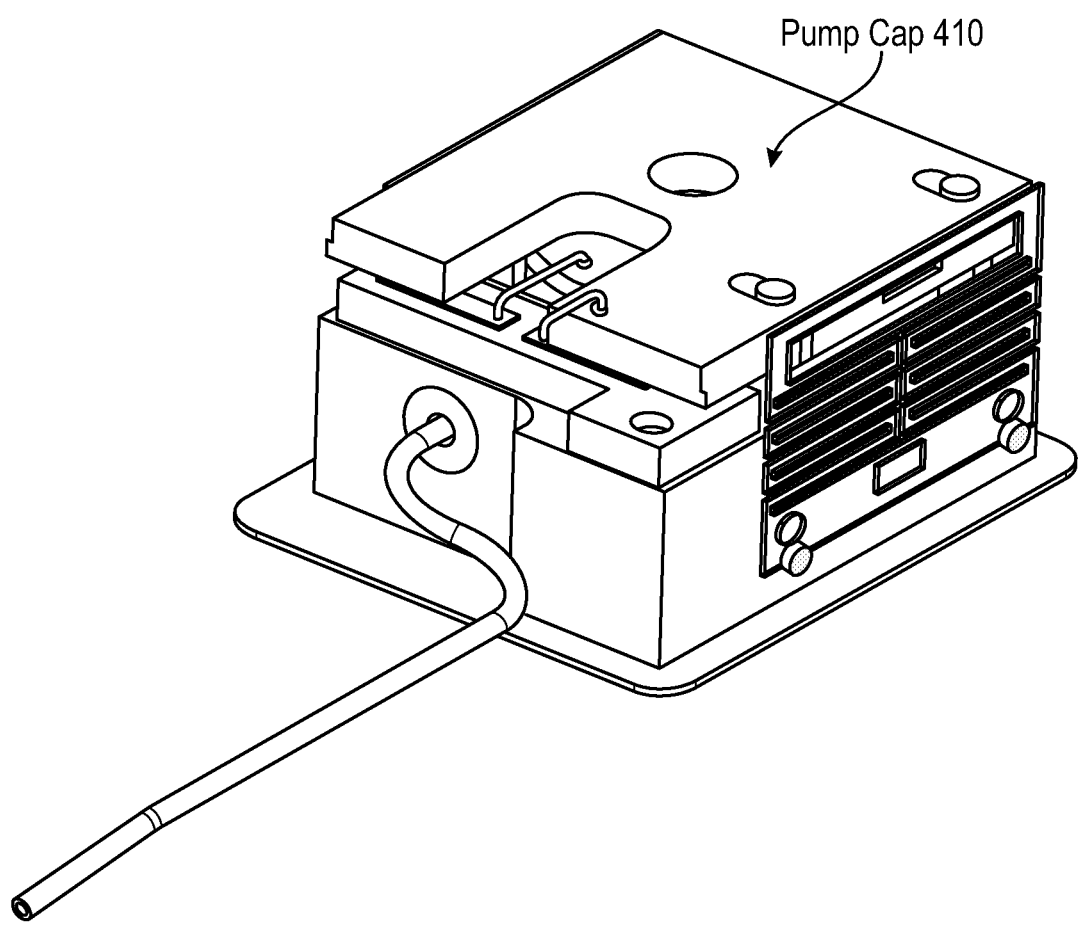
FIG. 4 depicts a perspective view of the MEMS pump assembly as abstracted from the exemplary device and seen in isolation.
Figure 5:
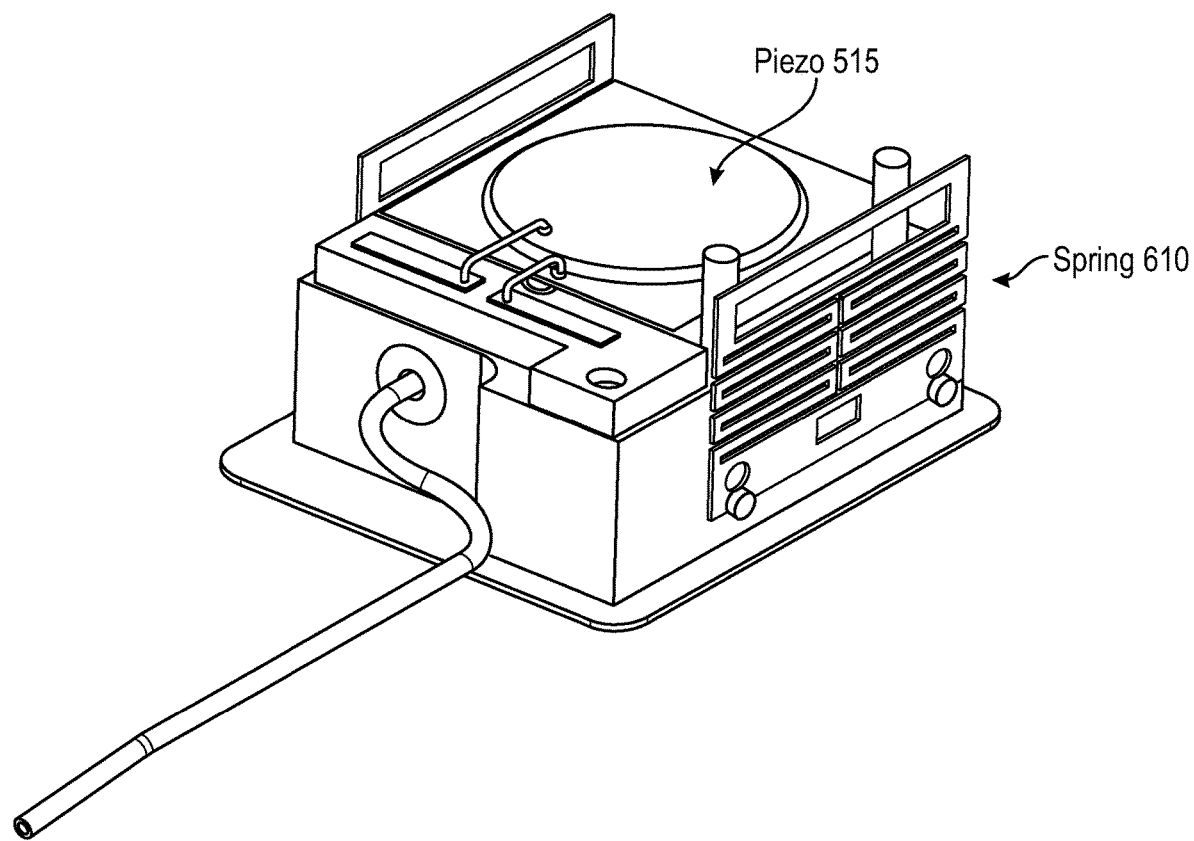
FIG. 5 depicts the exemplary MEMS pump of FIG. 4, with the pump cap removed, showing the piezoelectric actuator, in accordance with various embodiments.
Figure 6:
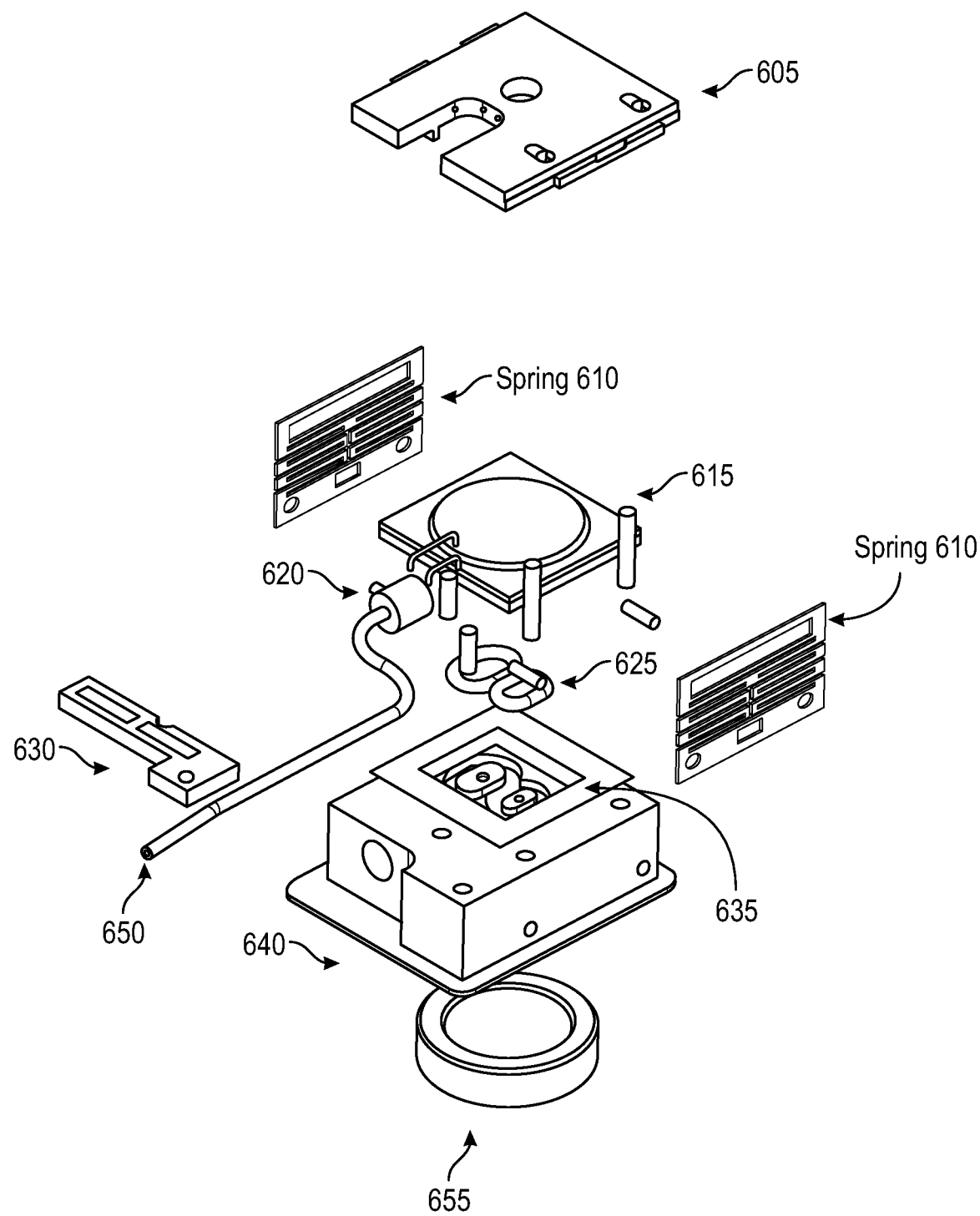
FIG. 6 depicts an exploded view of the MEMS pump assembly of FIG. 4
Figure 7:
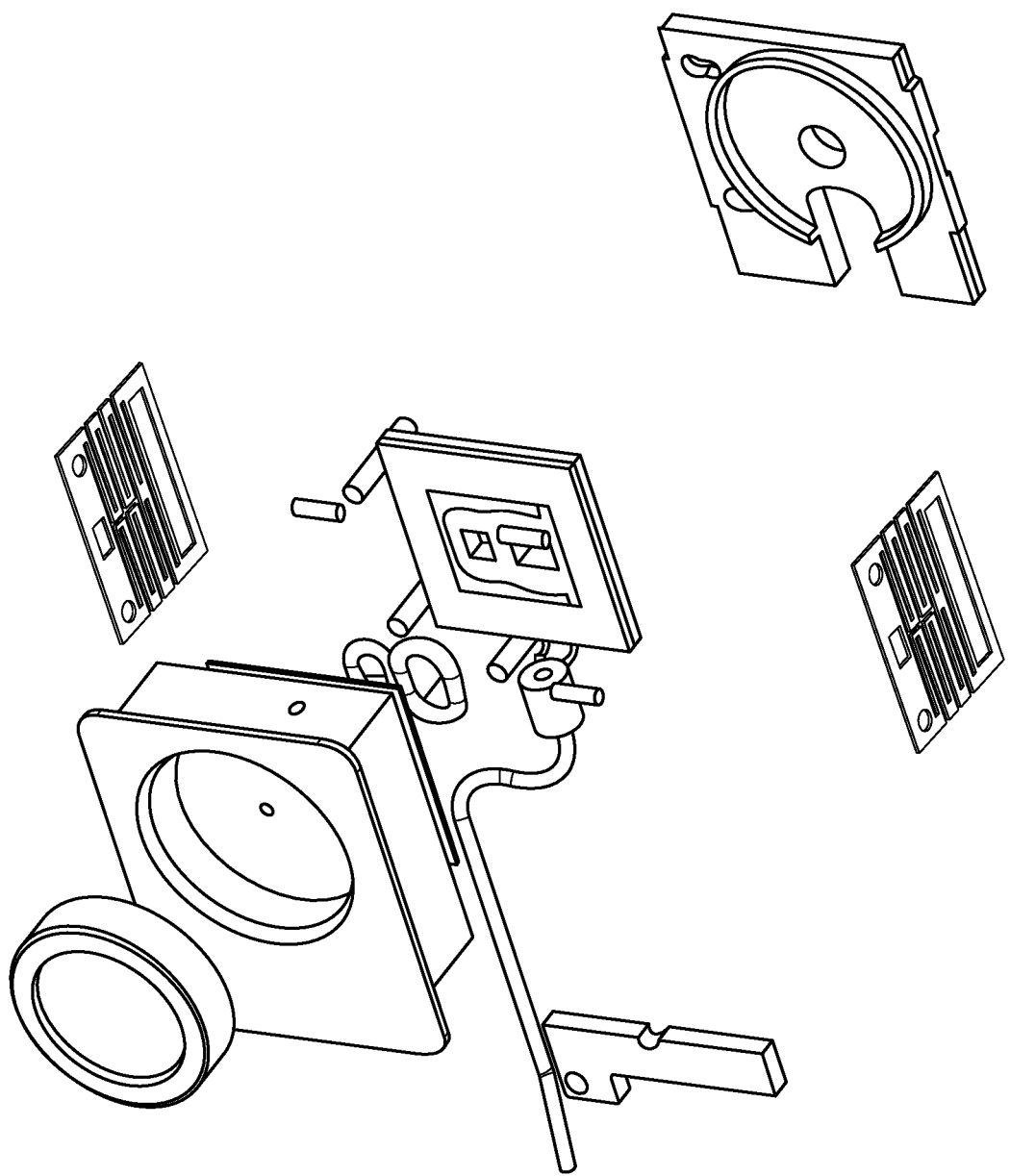
FIG. 7 depicts the exploded view of FIG. 6 from a perspective looking up from underneath the assembly.
Figure 8:
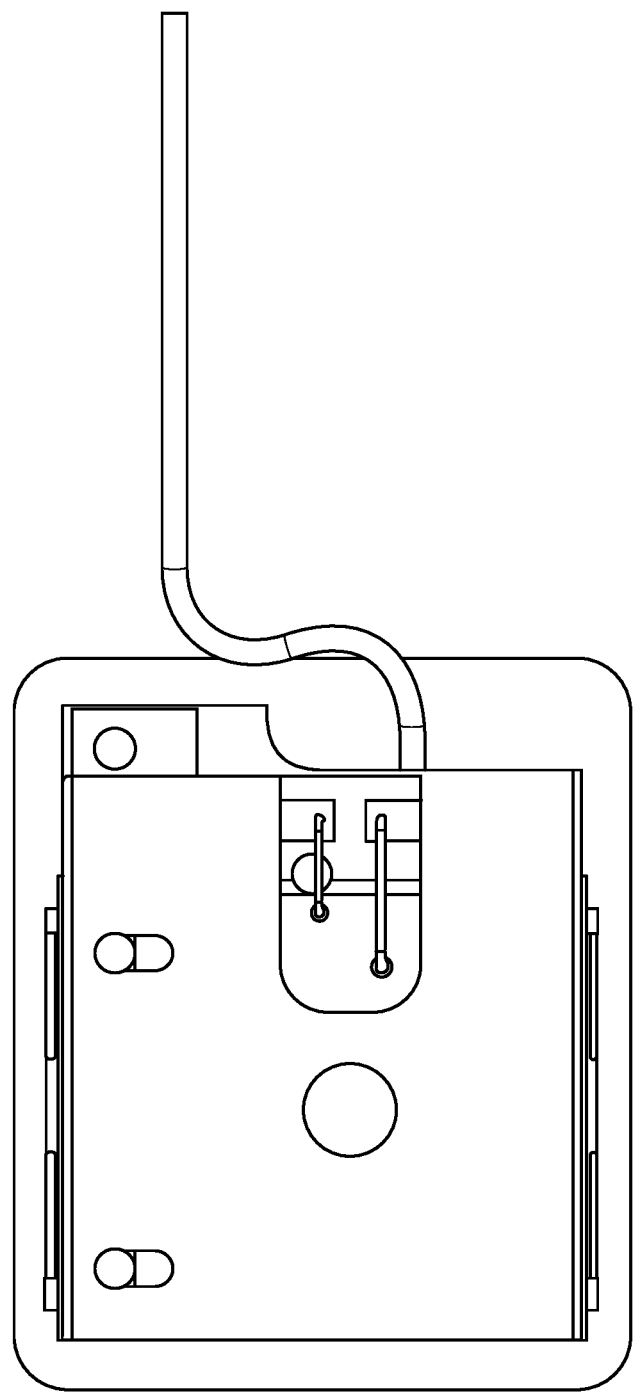
FIG. 8 depicts a top view of the exemplary MEMS pump assembly of FIG. 4.
Figure 9:
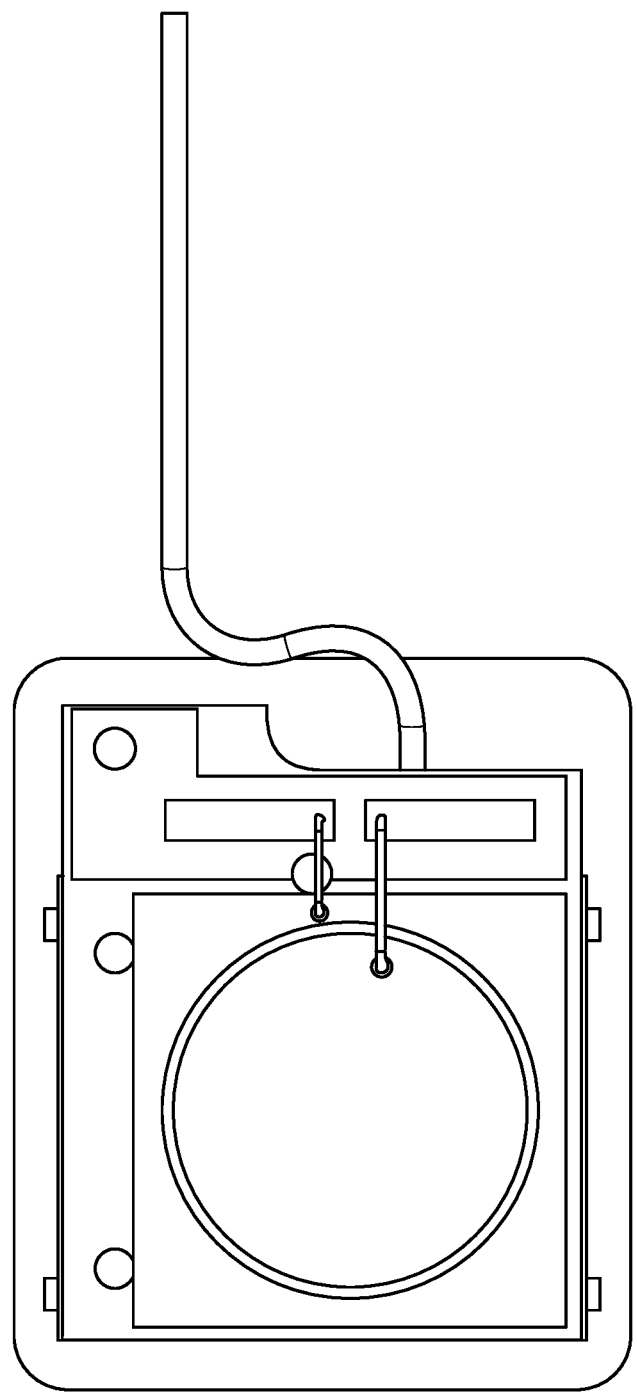
FIG. 9 depicts a top view of the exemplary MEMS pump assembly of FIG. 5, with the pump cap removed.
Figure 10:
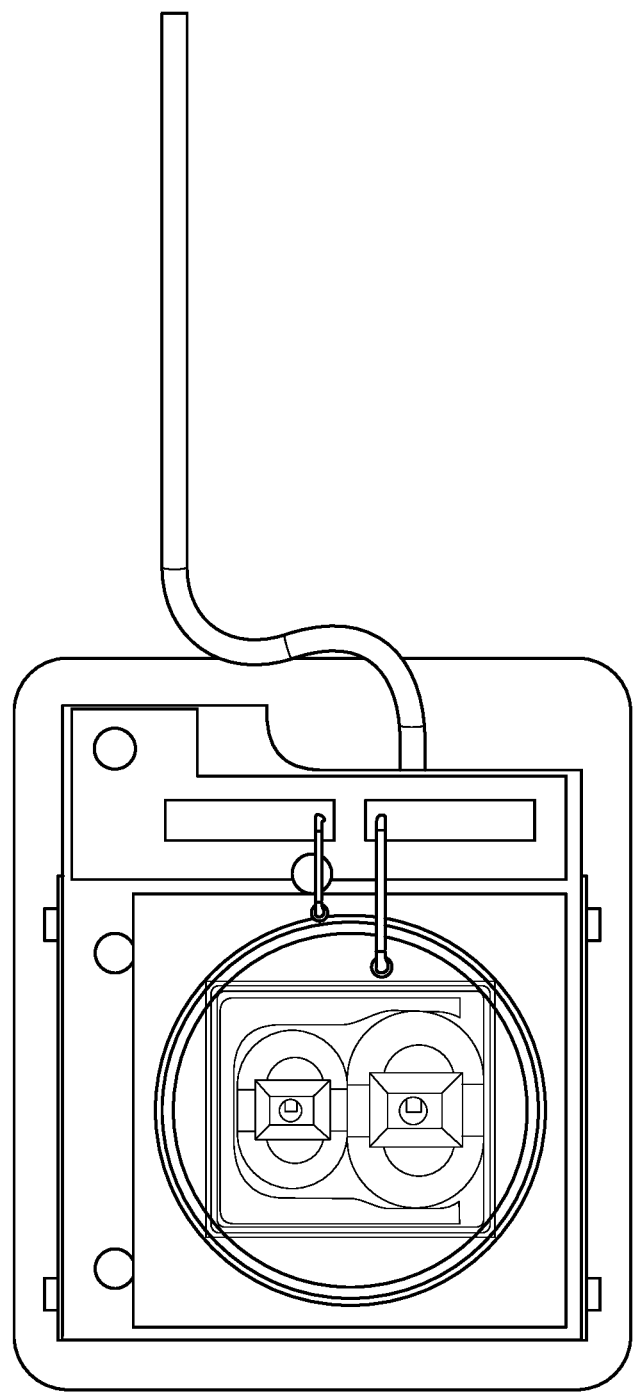
FIG. 10 depicts the view of the MEMS pump assembly of FIG. 9, with the piezoelectric MEMS micropump, including its piezoceramic actuator shown in transparency so that the components below may be seen (the pink frame is an exemplary solder preform)
Figure 11:
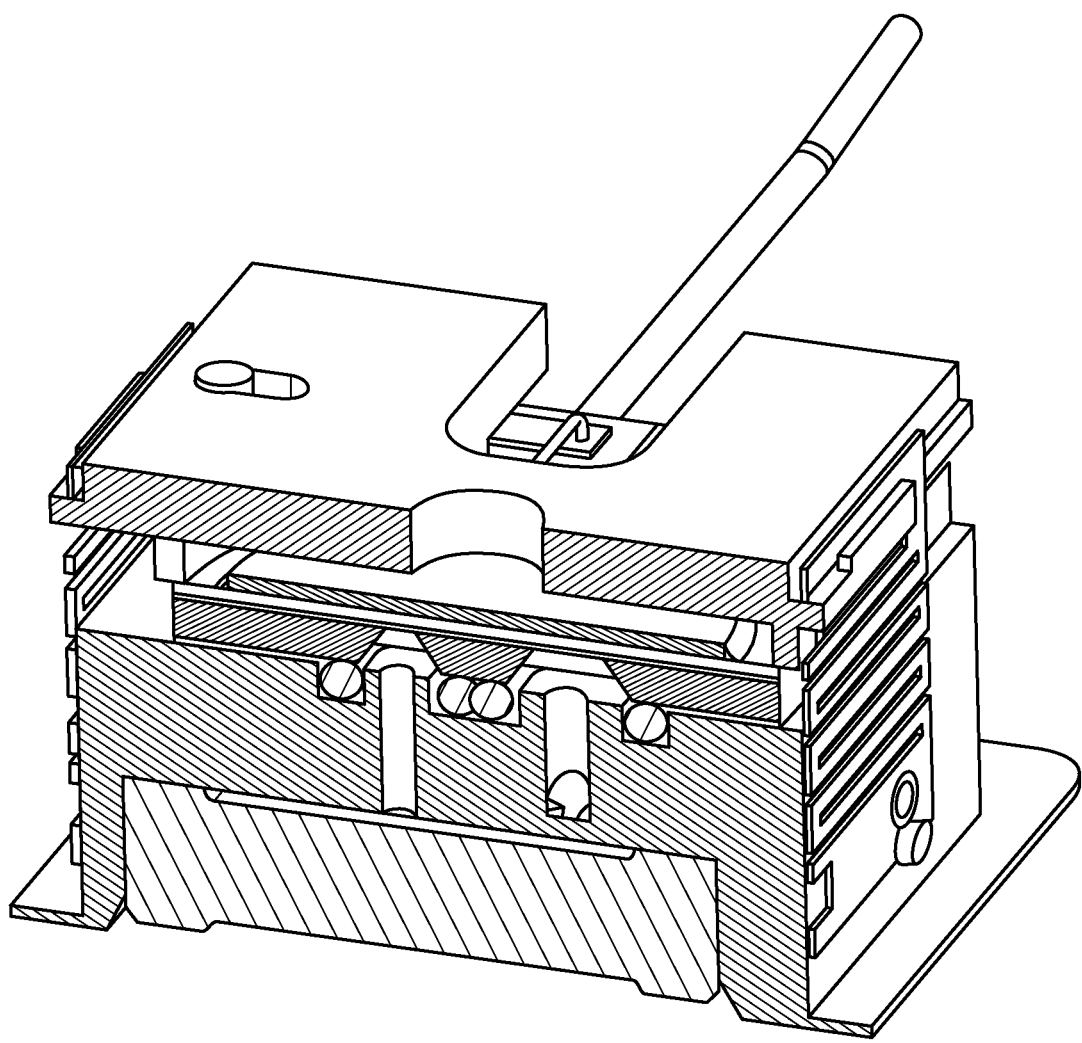
FIG. 11 depicts a rear view of the exemplary MEMS pump assembly of FIG. 4.
Figure 12:
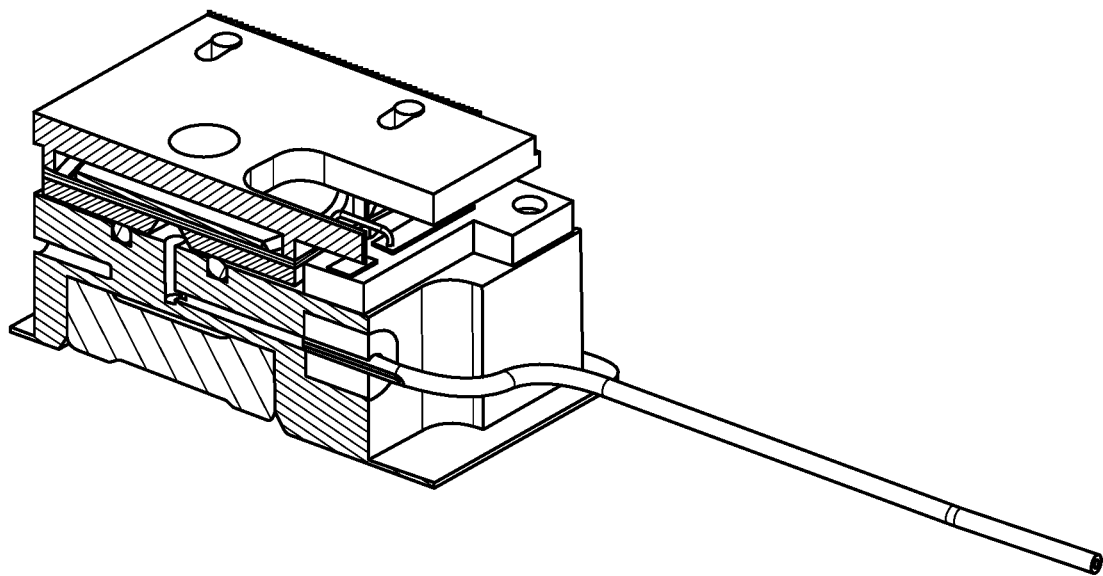
FIG. 12 depicts a front perspective view of the exemplary MEMS pump assembly of FIG. 4.
Figure 13:
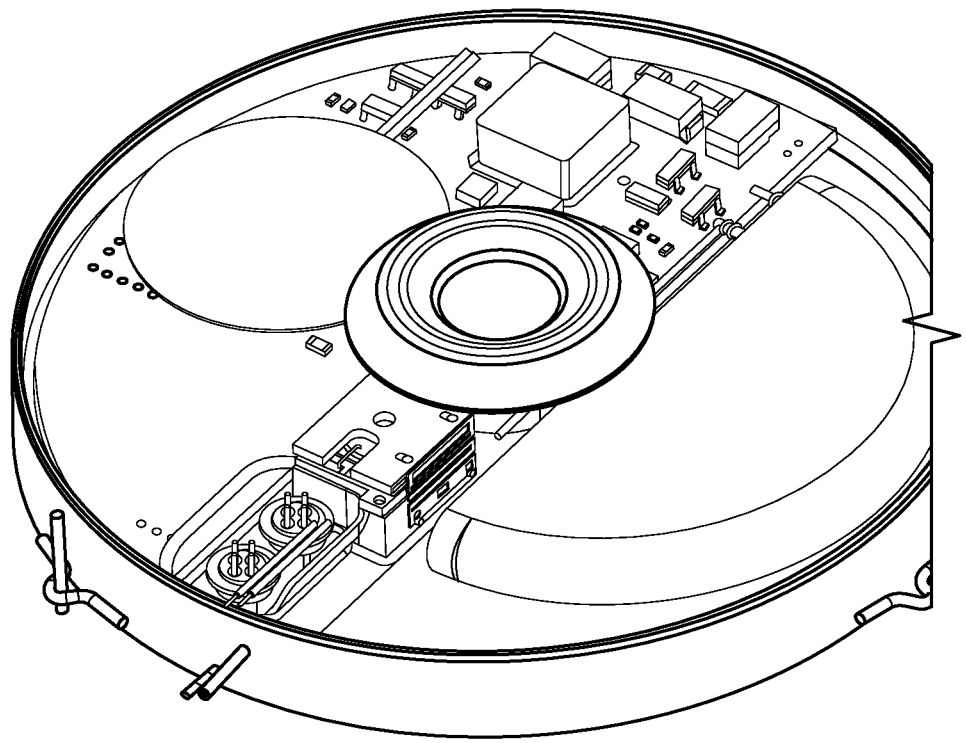
FIG. 13 depicts a perspective view of the exemplary implantable device from a point of view above the device and somewhat in front of it, where the large white disc is a piezoceramic tone transducer to produce audible alarms and alerts from the pump.
Figure 14:
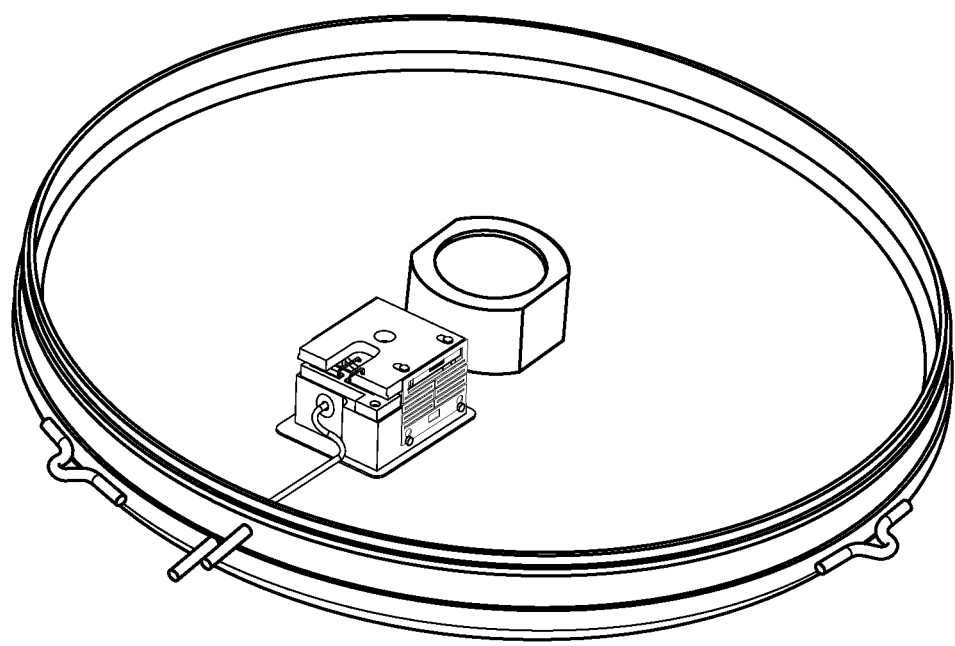
FIG. 14 depicts the exemplary MEMS pump assembly as positioned on top of the Medication Reservoir, with no other components shown (essentially the view of FIG. 13 with all other components on top of the Medication Reservoir removed)
Figure 15:
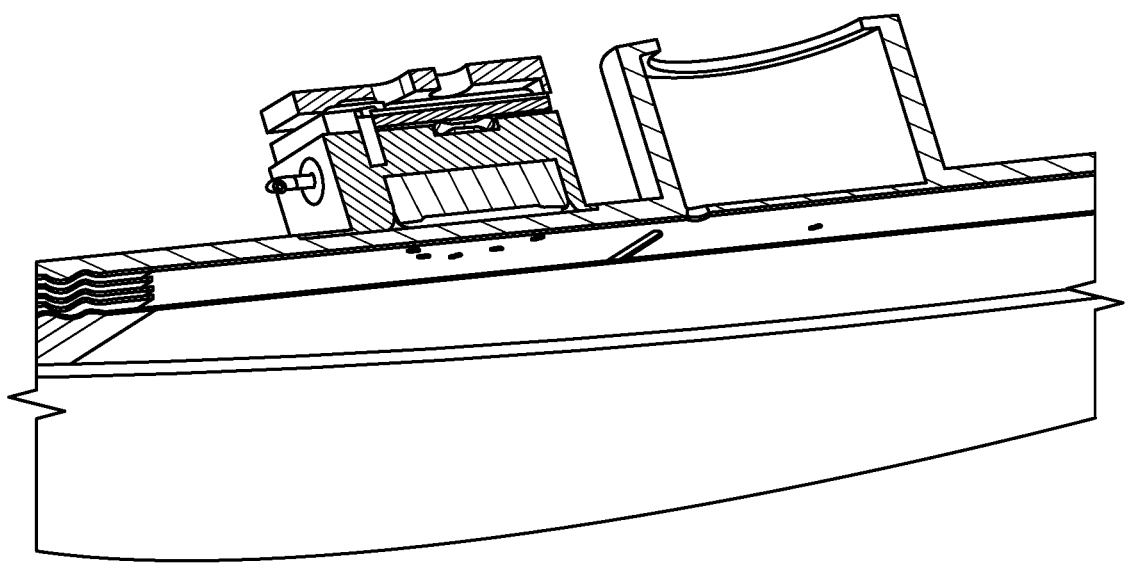
FIG. 15 depicts a side view into a vertical cut-away of the exemplary device of FIG. 14, where the vertical slice was made through the center of the device—and through one half of the MEMS pump assembly, allowing a view into the reservoir and into the MEMS pump.
Figure 16:
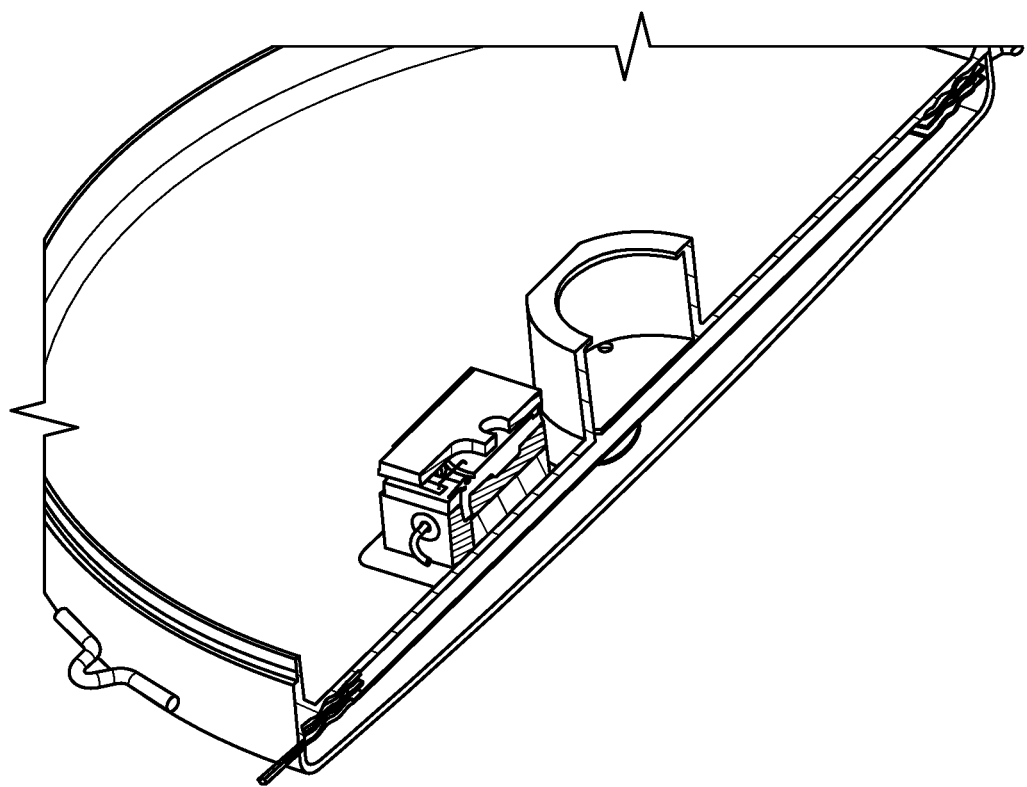
FIG. 16 depicts a top view of the cut away of FIG. 15.

As can be seen with reference to FIGS. 1-3, in the exemplary implantable device shown there is a MEMS chip 210 provided under a pump cap. As shown in FIG. 4, such a pump cap 410 may hold the piezoelectric actuator down (i.e., piezo 515 in FIG. 5, 615 in FIG. 6) and the pump cap may compress the double seal (in this embodiment achieved using O-rings) against manifold 640 (FIG. 6). Pump cap 410 may be made of aluminum, or for example, steel. While steel is a better choice because it is stiffer (notably, the Youngs modulus of Aluminum=$10\times10^6$ psi, whereas that of Steel=$30\times10^6$ psi) aluminum is less costly. In embodiments, the entire assembly may be pulled together by two springs 510, 610. These springs attach to the pump cap 410, shown in FIG. 4, and also to the manifold, as seen in FIG. 5. In embodiments they are designed to overcome the expansive force of the double O-ring seal as well as any force generated by injection of medication at high pressure into the medication reservoir—which would otherwise tend to put the solder joint under tension. With the springs in place, tension is thus precluded from the metallurgical joint between the MEMS chip and the manifold. In exemplary embodiments of the present invention, the O-ring can provide two seals between inlet and outlet, as shown in FIG. 10, for example.

FIG. 6 depicts in detail various parts of a MEMS pump according to embodiments. FIG. 6 is this an exploded view of the fully assembled MEMS pump as shown in FIG. 4. Referring to FIG. 6 there are shown a Pump Cap 605, which, as noted above, fits over the MEMS pump assembly, as shown in FIG. 4. In particular, Pump Cap 605 sits on Piezoelectric Actuator 615, which itself is mounted on Manifold 640, with, for example, an Indium Preform 635 between them, the latter used to solder the two surfaces together after the preparations as described below. Springs 610 also connect the Pump Cap 605 to Manifold 640, as shown in FIG. 4, and also as seen from a top view in FIG. 8, and a side perspective view in FIG. 11. Theses springs push Piezoelectric Actuator 615 and Manifold 640 together, which, as noted above, overcomes the expansive force of the double O-ring seal between them, as well as any force generated by injection of medication at high pressure into the medication reservoir—which would otherwise tend to put the solder joint between the two under tension. Finally, there are also shown Pre-filter 655, Outlet Fitting 620 and Outlet Tube 650, as well as Circuit Connection Board 630. These various parts are also shown in various perspectives, in various stages of attachment, or in various sectional views, in the remaining FIGS. 7-17.

Joining Silicon to Metal

As shown in FIGS. 1-17, an exemplary MEMS pump is joined to a manifold. It is here noted that this joining presents a significant challenge, in joining a silicon part (MEMS) to a titanium part (manifold) and not having the two components break apart due to CTE mismatch. As noted above, to the inventor's knowledge, in every case where such joining was attempted, the effort failed precisely because of the thermal expansion co-efficient mismatch. For example, one such effort is described in Kager, Simone, *Verbindungstechnik für die hermetische Einkapselung eines fluidischen Augenimplantats*, Masterarbeit am Lehrstuhl für Medizintechnik der TU München in Zusammenarbeit mit von Frau Simone Kager, Matrikelnummer: 3601768, Studienfach: Maschinenwesen (Sep. 30, 2014). In the attempts to join silicon and titanium therein described, the CTE mismatch was an insurmountable obstacle. Thus, the bond between the silicon and the titanium failed spontaneously, and the device just blew apart and broke. The present disclosure solves this problem with a novel process, next described.

The CTE mismatch between any two materials is amplified by the temperature excursion through which they are taken. Thus, the key to solving this problem is to find a solder that melts at a sufficiently low temperature such that the temperature excursion In exemplary embodiments of the present invention, the two components—metal and silicon—may be joined by performing a soft solder joint using indium silver. In embodiments, the solder may comprise 97% Indium and 3% silver, for example, which results in a very low temperature solder. It is also actually fairly soft, and may thus accommodate any strain generated due to CTE mismatch. The temperature excursion from a room temperature of 25° C. to the solidus point of the solder (for Indium-silver solidus is at 143° C.) which is needed to melt the solder is not enough to develop a lot of strain between the two surfaces, which is a key consideration in choice of solder. See, for example, http://www.indium.com/solder-alloy-guide/results.php (Indalloy #290); http://www.cleanroom.byu.edu/CTE_ materials.phtml, http://www.indium.com/solder-alloy-guide/results.php (Indalloy #290). It is noted that solidus is the highest temperature at which an alloy is still completely solid.

Strain Acting Through the Solder Joint

It is also noted that the actual stress in the solder is inversely proportional to the solder thickness, and requires a calculation of the stress map of the sandwich. It may thus take into account the CTE of the solder, 22 ppm.

The coefficient of thermal expansion is often defined as the fractional increase in length per unit rise in temperature. It is noted that the exact definition varies, depending on whether it is specified at a precise temperature (true coefficient of thermal expansion or a-bar) or over a temperature range (mean coefficient of thermal expansion or a). It is noted that the true coefficient is related to the slope of the tangent of the length versus temperature plot, while the mean coefficient is governed by the slope of the chord between two points on the curve. Accordingly, variation in CTE values can occur according to the definition used. When a is constant over the temperature range then a=a-bar. Finite-element analysis (FEA) software such as, for example, NASTRAN (MSC Software) requires that a be input, not a-bar.

The following example calculation illustrates shear strain acting through solder in a example Titanium to Silicon soldered joint using indium-silver solder, in accordance with various embodiments:

Calculate the CTE Difference Between the Two:

Ti 9.5 CTE (ppm/° C.)–Si 2.6 CTE (ppm/° C.)=6.9 ppm/° C. difference in CTE 6.9*$\Delta T$=6.9*[143 C (solidus)–25 C (room temperature)]=C*118 degrees 6.9 ppm/degrees×118 degrees=814 ppm difference in normal strain between the silicon and the titanium.

It is noted that the difference in displacement is a maximum at the edges. Moreover, the strain is generally equal and opposite for each edge, so that the relative displacement at the center is 0. For this reason, in embodiments, the relative displacement may be calculated using half of the width of the chip, or 3.5 mm.

Using the 814 ppm figure derived above:

0.0814 percent×3.5 mm=3.5×0.0814=0.00285 mm or 2.85 microns.

In embodiments, a preferred thickness for a solder joint may thus be 25 to 250 microns. Thus, for a device that is a square with a length of 7 mm per side, and with a solder joint thickness of 25 microns, shear strain would be arc tan (relative displacement/thickness). Shear strain is thus the infinitesimal angular displacement of any element in the solder:

Shear strain=arc tan(2.84/25)=0.1113 radians.

It is noted that an elastic calculation of the stress level may generate a stress in excess of the yield strength for the solder material (approximately 400-600 psi for the example In97 Ag3 solder provided by the Indium Company used in tests run by the inventor). Thus, in embodiments, actual stresses may be derived experimentally. It is noted that for the example In97 Ag3 solder used in tests run by the inventor, the elongation to break in tension solder was seen at 50%. The empirical information thus supports a 10 mil thickness of In97 Ag3 for packages less than 10 mm in dimension, as per the Indium Corporation, the manufacturer of the example solder used.

Soldering to Each of Titanium and Silicon

A. Preparing the Silicon Surface

Having chosen a low temperature solder and a desired thickness of the solder joint, a technical problem remains as to how one solders to titanium and to silicon. As is known, neither of these elements will wet or adhere to known soldering materials. In embodiments, this may be accomplished as follows. First, the silicon oxide coating on the MEMS chip (this coating is always on any silicon surface) may be removed using a hydrofluoric acid. Preferably, using Buffered Hydrofluoric Acid, which typically contains 30-50% Ammonium Fluoride and 5-10% Hydrofluoric acid. Second, one takes and sputters the joining surface of the MEMS micropump—quickly, before the SiO2 surface reforms—with titanium tungsten, which is an adhesion promoter. Alternatively, treatment with hydrofluoric acid may be omitted if the joining surface of the MEMS micropump is sputtered with titanium silicide. This is because the Titanium silicide breaks up the silicon oxide.

Finally, in embodiments, a layer of nickel may be deposited. However, because nickel will form an oxide layer upon storage in air, and thus not wet to solder, gold is added to protect the nickel surface. During soldering, the gold layer dissolves into the solder—leaving a fully wetted nickel-solder interface. Thus, one ends up with a clean bottom surface on the MEMS chip of titanium tungsten (Ti—W), nickel and gold. It is here understood that it is actually the nickel that is being soldered to, the gold merely protecting the nickel from oxidation.

Still alternatively, in embodiments, the titanium tungsten may be omitted, and following the treatment of the silicon pump surface with hydrofluoric acid, a layer of nickel may be deposited, followed by a layer of gold.

B. Preparing the Titanium Manifold Surface for Soldering:

Having prepared the silicon pump surface, next described is preparation of the titanium manifold surface. Titanium metal forms a dense stable oxide which does not wet to solder. Therefore, in order to create a surface that will wet to solder, in embodiments, the surface of the titanium may be ground flat with a 1000 grit finish, and electroless nickel plated onto the titanium. Electroless nickel makes a weak adhesive bond to titanium oxide. Therefore, in order to achieve a strong metallurgical attachment of the nickel to the underlying titanium, the manifold with the nickel plating may be heated, for example, to about 400° C. for 30-60 minutes. At this temperature, the titanium oxide breaks down and the nickel alloys with the titanium, resulting in a transition zone on the top of the manifold from titanium to nickel titanium alloy to a pure nickel surface.

In embodiments, in order to protect the nickel surface from oxidation, as described above in the preparation of the silicon MEMS pump, the manifold may be further coated with gold. This process may be performed, for example, in a sputtering chamber. To do this, the nickel surface is first cleaned with an ammonia containing cleaning agent and then sputtered with another layer of nickel, and finally, a layer of gold. The additional layer of nickel is added because sputtered nickel adheres well to nickel, even with a small amount of oxide. So, in embodiments, a second layer of nickel may be sputtered onto the first layer in case the baking operation described above (of the electroless nickel plated onto the titanium) has created such a thick oxide that it is not easily wetted. Following the sputtering of the second layer of nickel, the manifold may be immediately gold plated.

Soldering the Treated Silicon Surface of the Pump to the Treated Titanium Surface of the Manifold Once both surfaces have been prepared, as noted above, a preform of indium silver, comprising three percent silver and ninety-seven percent indium, which has a very low melting point, may be used in a soldering operation in forming gas. Forming gas is a reducing agent and removes oxidation from any of the metallic surfaces. Generally, forming gas comprises 10% $H_2$ and 90% $N_2$, and this may be used for the soldering process. In embodiments, this temperature may be controlled to be in the range of 140° C. to 160° C. in order to:

Minimize the strain due to the CTE by limiting the temperature excursion;
Prevent depolarization of the piezo ceramic actuator (615 in FIG. 6) which occurs at approximately 200° C.; and
Prevent relieving the epoxy pre-stress that is part of the operational design of the actuator that occurs at temperatures above 160° C.

It is also noted that a filter may be loaded into the back of the titanium manifold, shown, for example at 655 in FIG. 6. In embodiments, the filter may be a 5u filter to prevent particle entry into the pump, and may, for example, be made from a large variety of polymers, metals or silicon.

Figure 17:
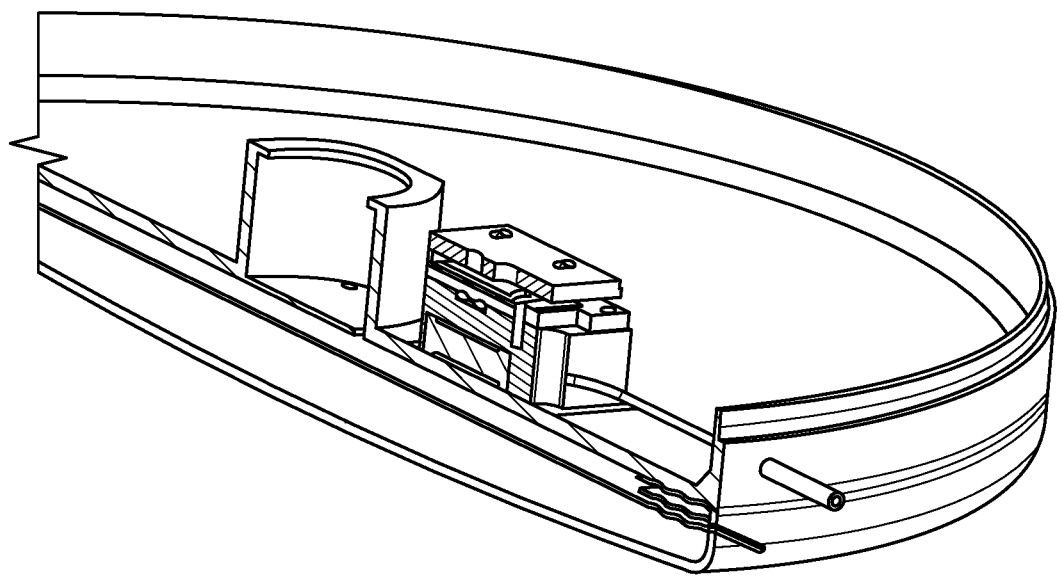
FIG. 17 depicts a cut-away of the exemplary device of FIG. 14, but here showing the other side of the device than is depicted in FIG. 16.
Figure 17A:
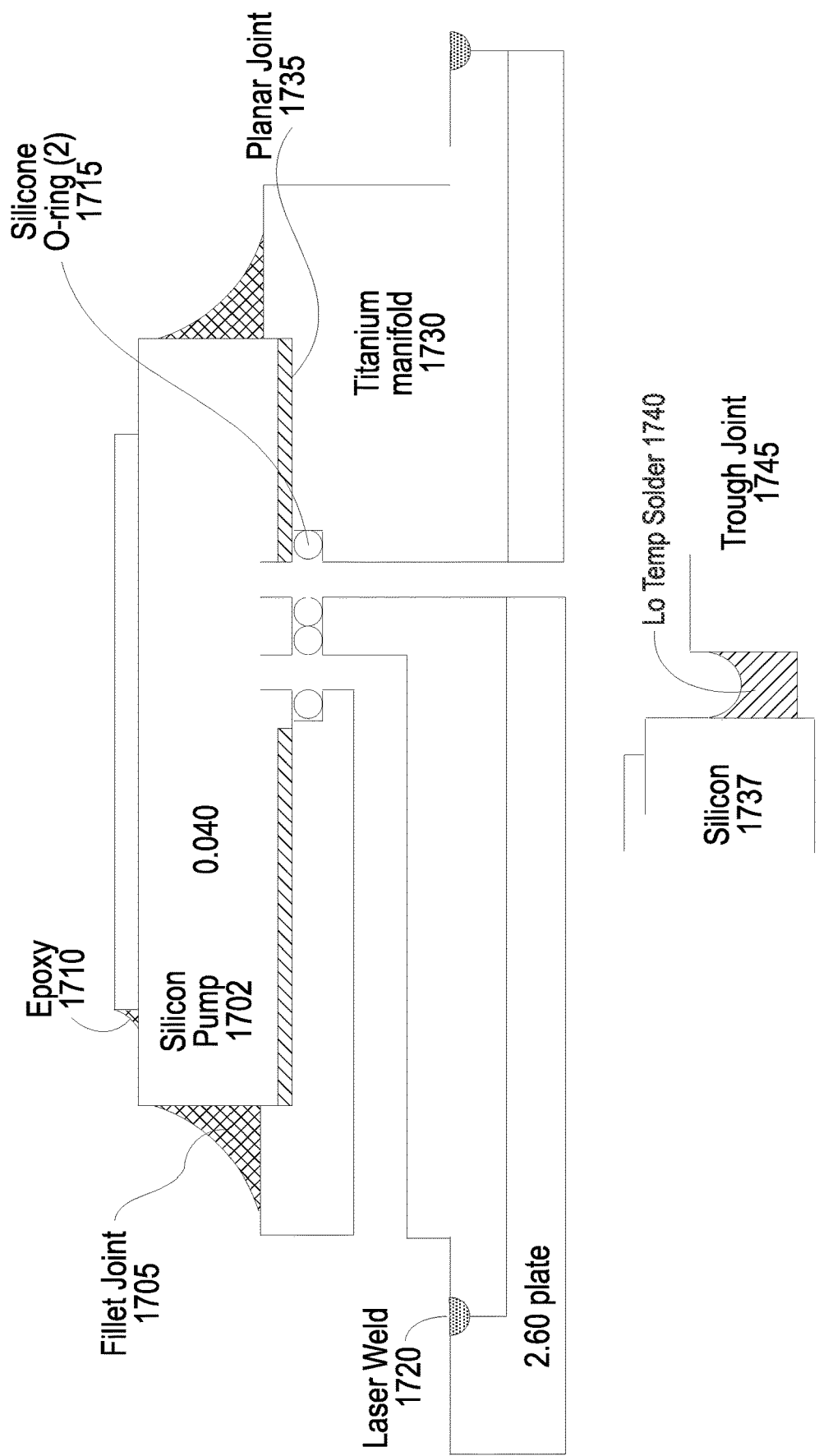
FIG. 17A illustrates three alternate joints that may be used to join an exemplary silicon pump to a Titanium manifold, in accordance with various embodiments.

FIG. 17A is a vertical cross-section of a Silicon Pump 1702 joined to a Titanium Manifold 1730 according to an embodiment. It illustrates three alternate joints that may be used in embodiments to join Silicon Pump 1702 to Titanium Manifold 1730. These may be, with reference to FIG. 17A, a fillet joint 1705 or a planar joint 1735. Alternatively, as shown at the bottom of the figure, a trough joint 1745 may be used to join Silicon 1737 to the titanium manifold. It is noted that the advantage of the fillet and the trough designs is that the titanium, which has a greater CTE than silicon, as noted above, (CTE for Ti of 9.5 ppm/° C. versus 2.6 ppm/° C. for Si) will shrink around the indium solder and the silicon MEMS pump, thus putting the silicon and titanium interfaces (as prepared) in compression, and as a result, there will be no force tending to separate the pump from the manifold. However, the fillet joint places shear stress on the titanium solder joint. The trough has no surfaces with shear or tension. As a result, the springs and pump cap may be eliminated in these designs. However, the sputtering process, which is line of sight, may be more difficult for trough joints. As may be seen in FIG. 17A, between the pump and manifold are provided two O-rings 1715, one surrounding the inlet (right side, vertical), the other surrounding the outlet (left side, with 90 degree elbow).

Figure 17B:
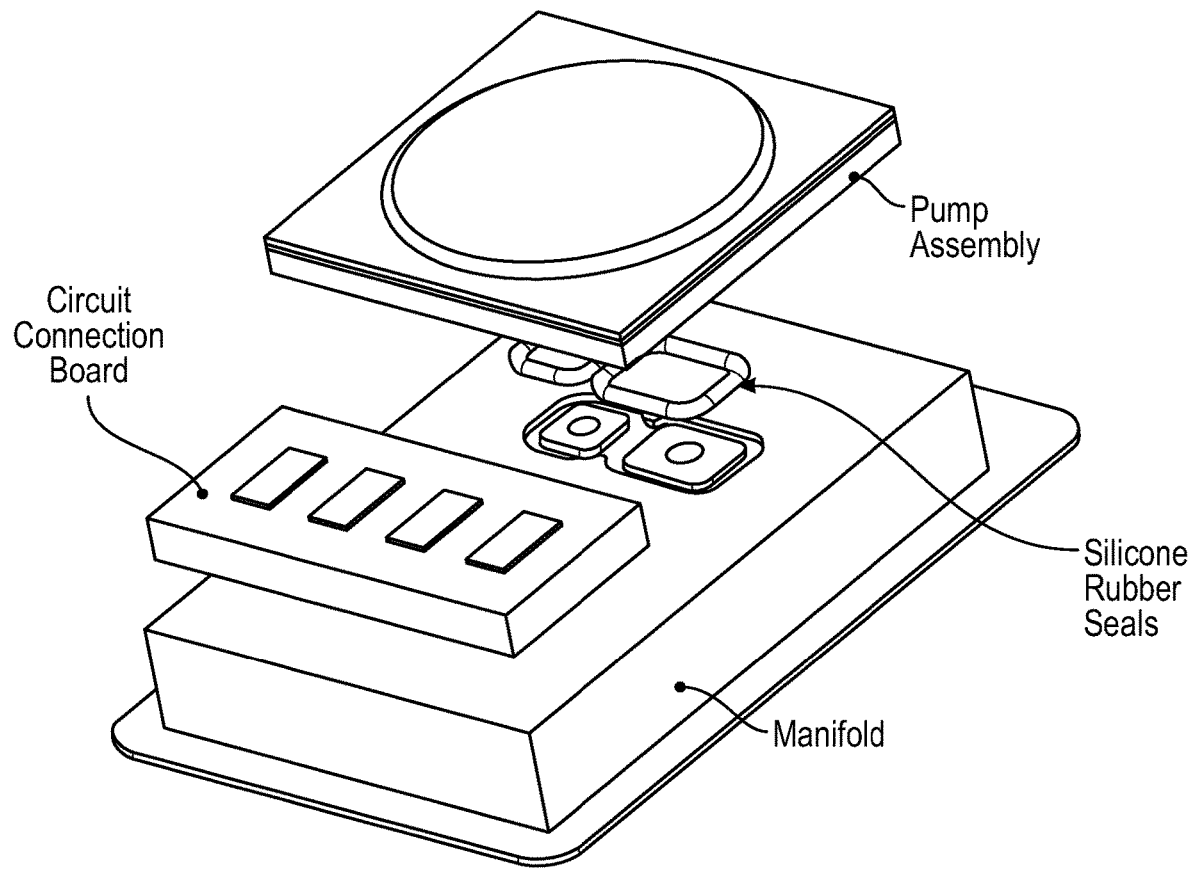
FIG. 17B depicts an exploded detail view of a pump assembly, O-rings, manifold and circuit connection board, in accordance with various embodiments.

FIG. 17B depicts an exploded detail view of a pump assembly, O-rings, manifold and circuit connection board according to an exemplary embodiment of the present invention.

Figure 17C:
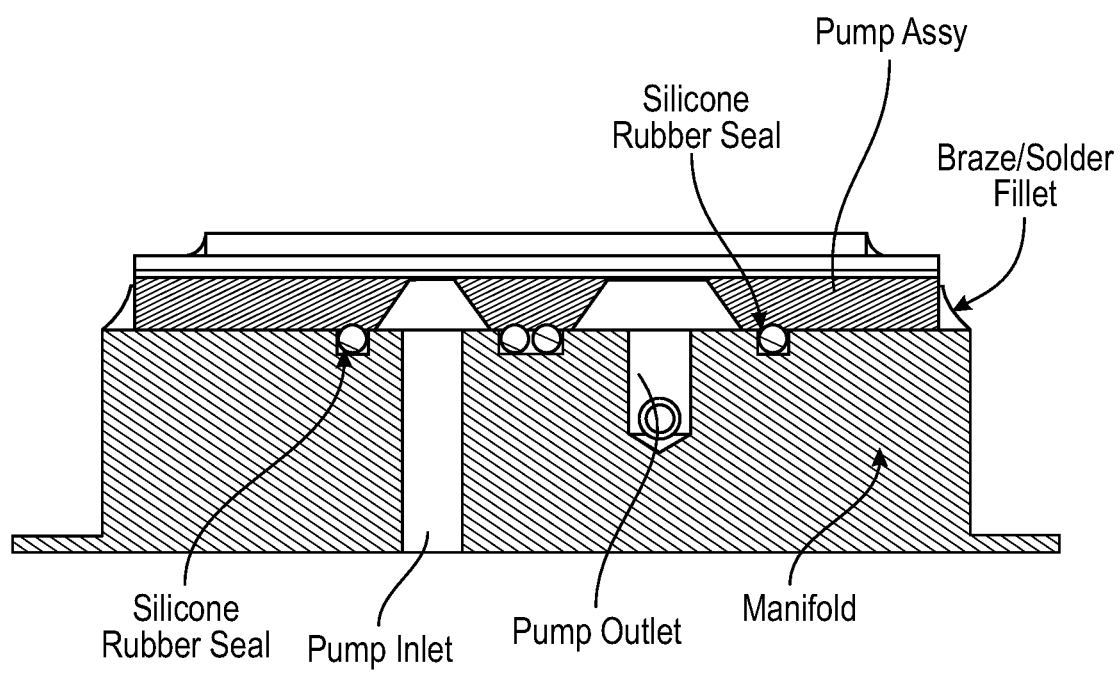
FIGS. 17C through 17E illustrate further details of each alternate joint of FIG. 17A, in vertical cross-sectional views.
Figure 17D:
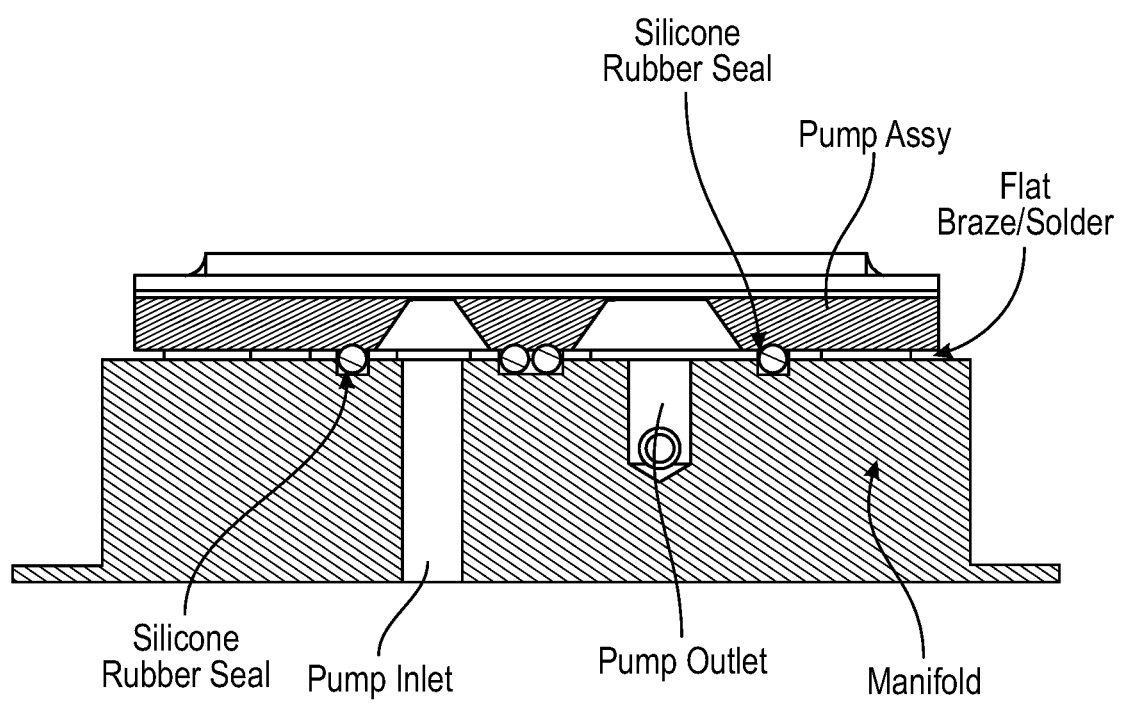
Figure 17E:
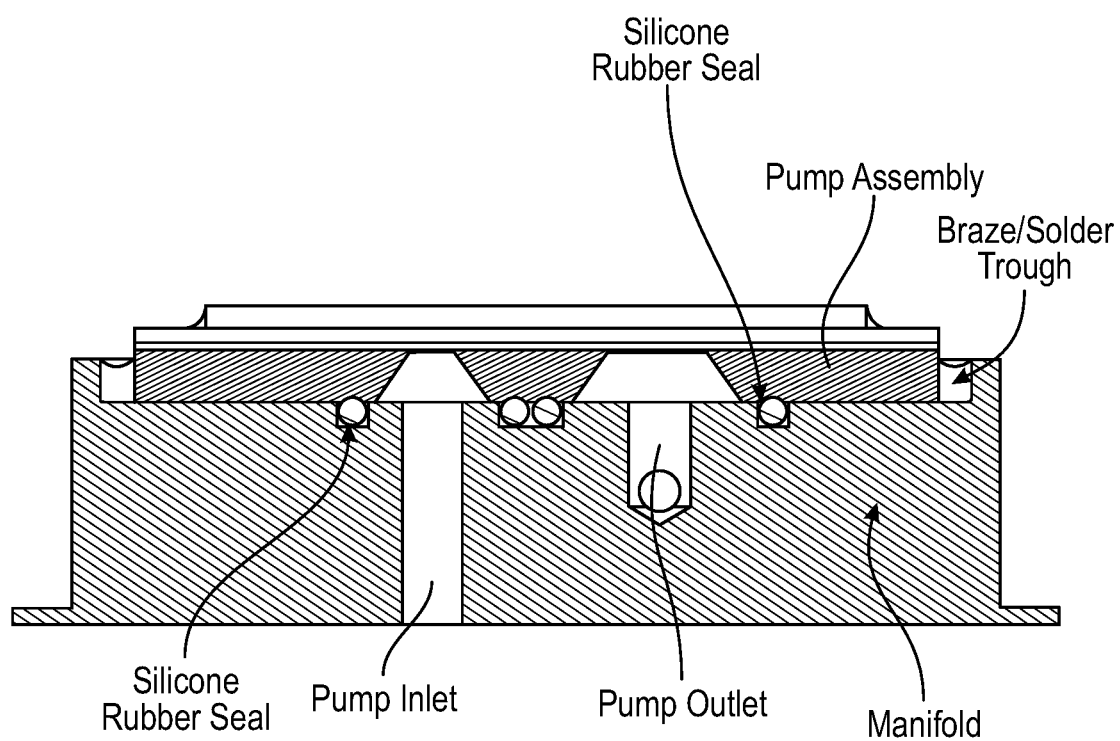

FIGS. 17C through 17E illustrate further details of the three alternate joint types shown in FIG. 17A, shown in a vertical cross section through an exemplary pump assembly and manifold joined together. FIG. 17C illustrates the fillet type joint, FIG. 17D the planar or flat joint, and FIG. 17E the trough type joint.

Figure 17F:
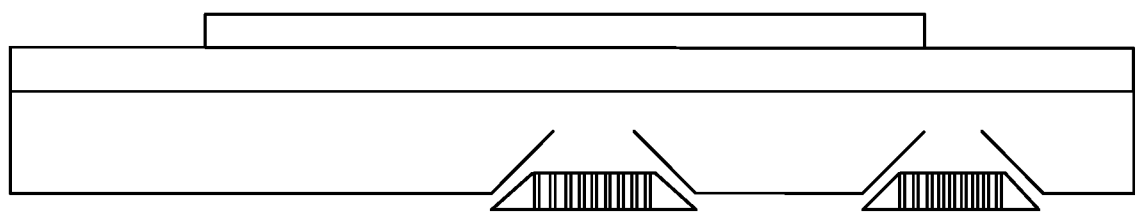
FIG. 17F illustrates exemplary inlet and outlet filters for a MEMS pump.
Figure 17G:
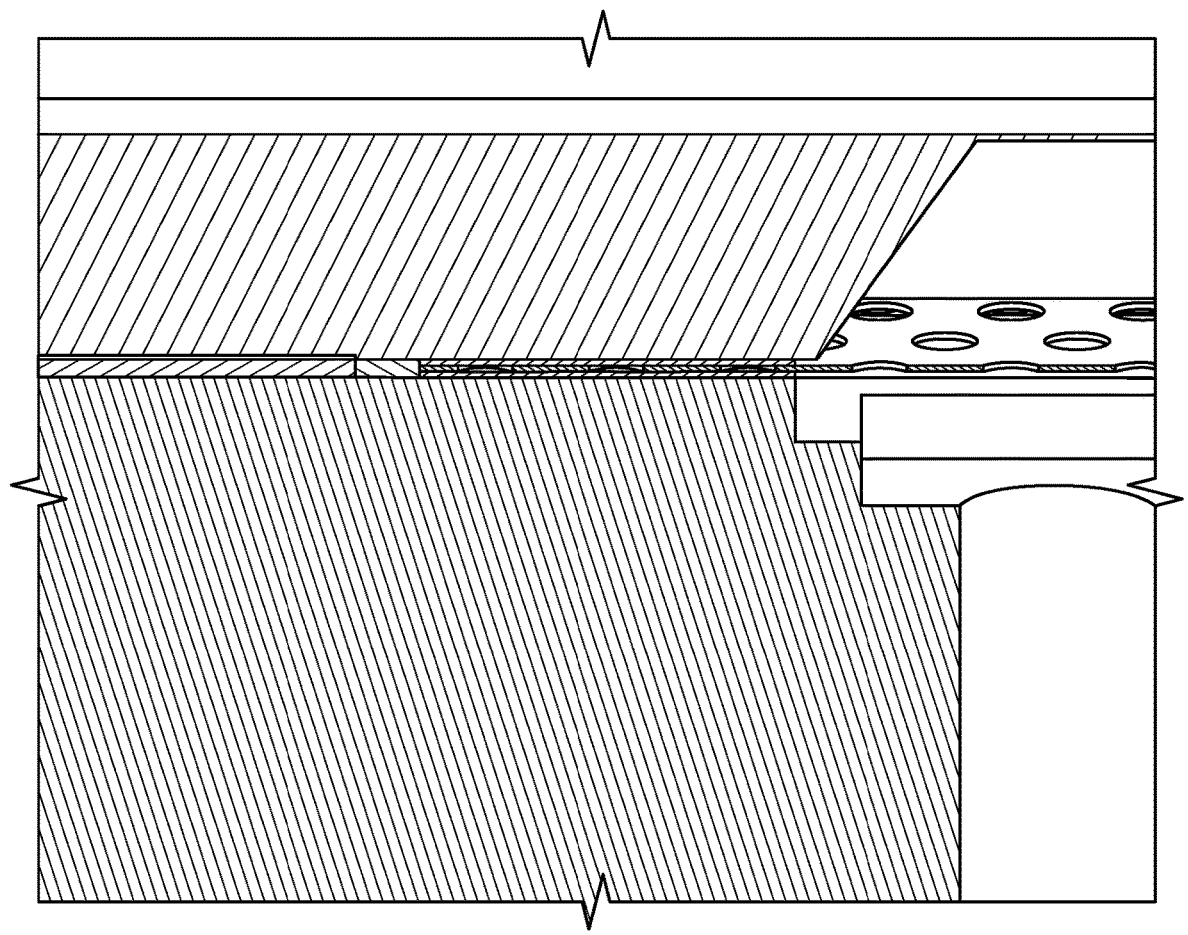
FIGS. 17G and 17H illustrate an alternate embodiment using an adhesive (dispensed or pressure sensitive layer) to attach a filter, thus providing an alternative to the O-rings used in the embodiment shown in FIGS. 1-17.
Figure 17H:
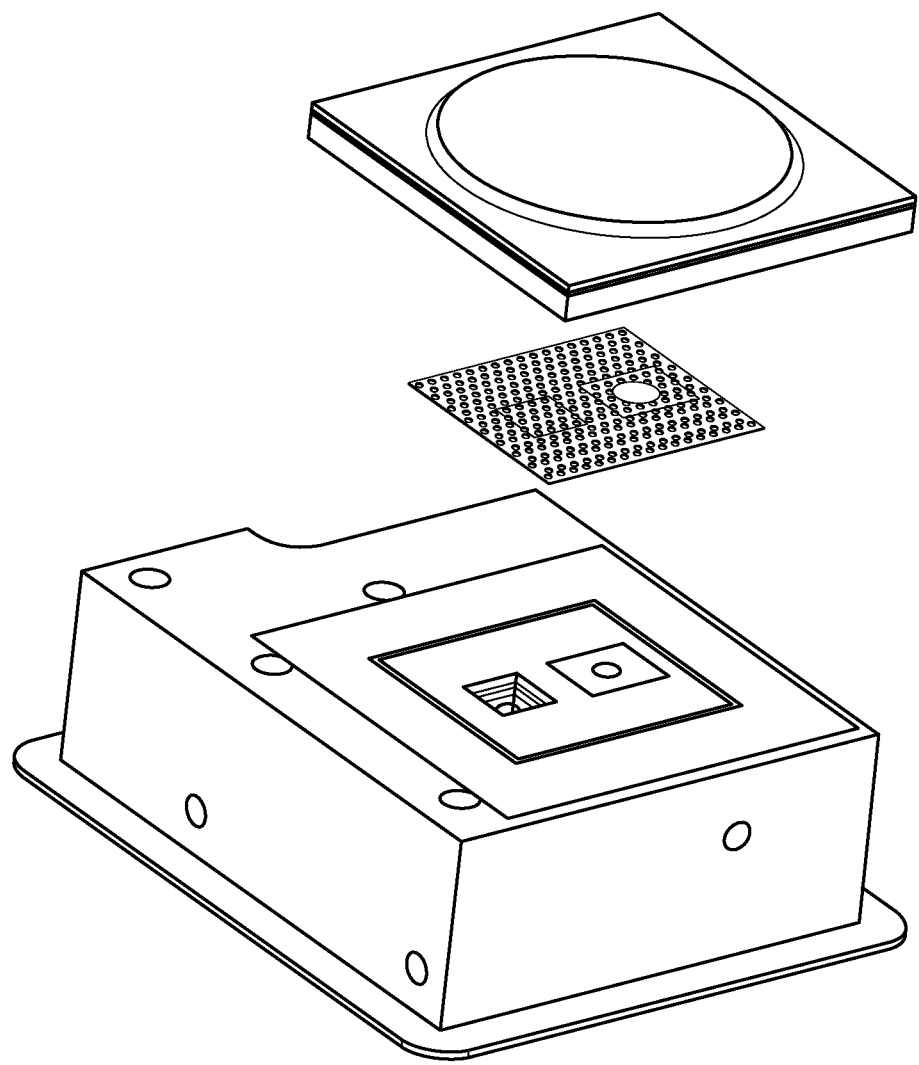

Referring now to FIG. 17F, this illustrates exemplary inlet and outlet filters for a MEMS pump according to embodiments. In embodiments, these stay sealed from the moment the pump is built in a clean room.

FIGS. 17G and 17H illustrate an alternate concept for a configuration using an adhesive (dispensed or pressure sensitive layer) to attach a filter and replace the O-rings in the embodiment shown in FIGS. 1-17E, In embodiments, the filter may be polycarbonate, polyether sulphone, or alternatively, a polyamide etched track filter with 5 micron holes or smaller. In embodiments, the adhesive may be silicone or acrylic based. As may be seen in FIG. 17G, the preform (Indium silver) may be thicker than the adhesive layer.

FIG. 17H depicts the example of FIG. 17G in a top perspective view. In embodiments, there may be two separate inlet and outlet adhesives (with filters). This allows each flow path to be tested separately.

Figure 17I:
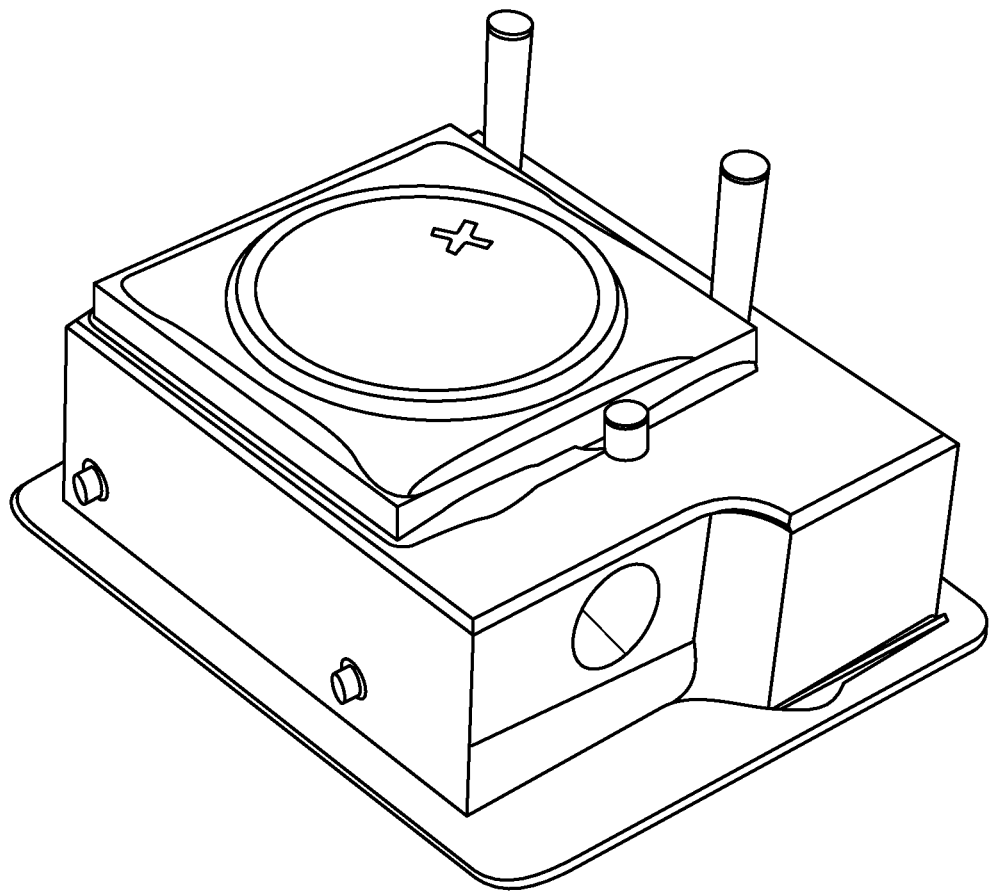
FIG. 17I is a photograph of an actual MEMS pump attached to a titanium manifold, in an embodiment similar to that of FIGS. 1-17, shown here without the springs or pump cover.

FIG. 17I is a photograph of an actual MEMS pump attached to a titanium manifold, in an embodiment similar to that of FIGS. 1-17, without the springs or pump cover. The depicted device is similar to the view shown in FIG. 5, but without the springs, and easily seen is the gold plating on the manifold's upper surface, as well as the solder joint around the periphery of the pump assembly. This example used a trough joint.

Figure 18:
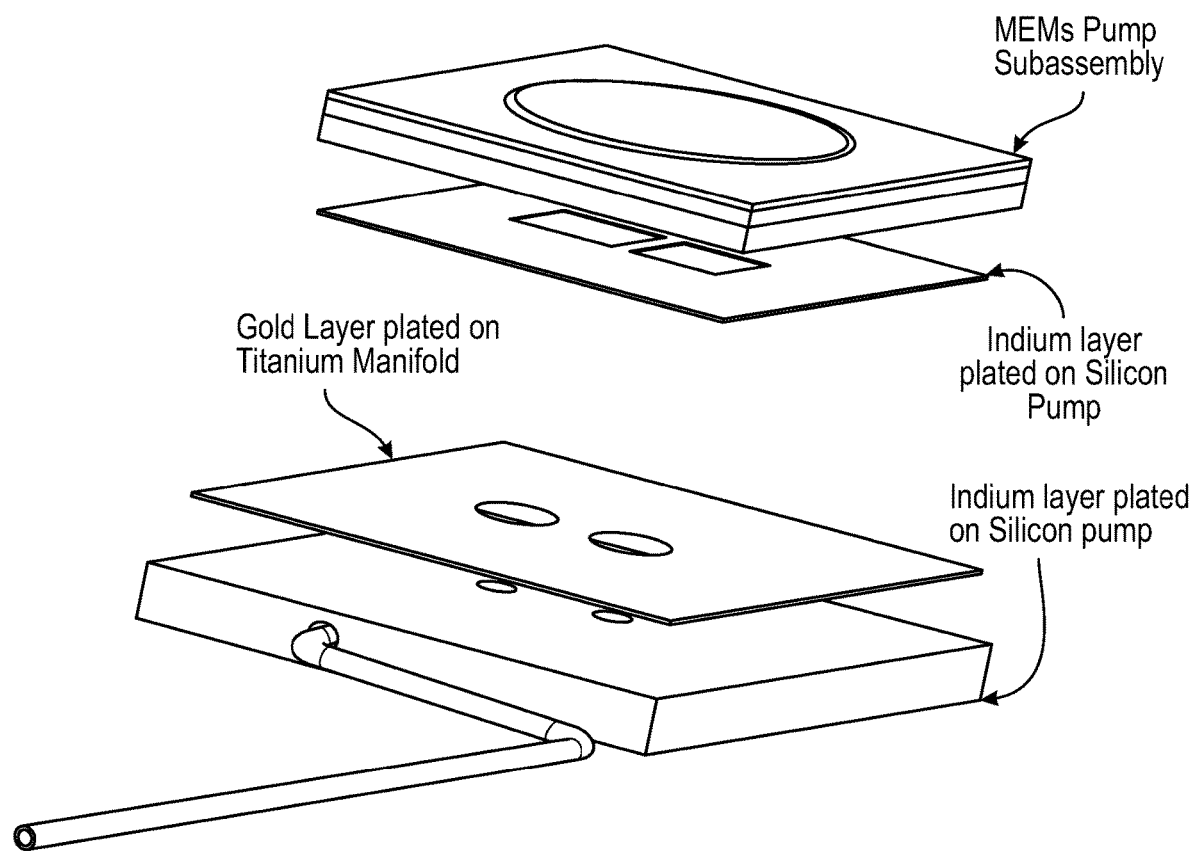
FIG. 18 depicts an alternate example of attaching a MEMS pump to a titanium manifold, in accordance with various embodiments, showing the MEMS pump assembly on top and the titanium manifold on the bottom of the figure, each with a layer to be attached to the top and bottom surfaces to be joined.
Figure 19:
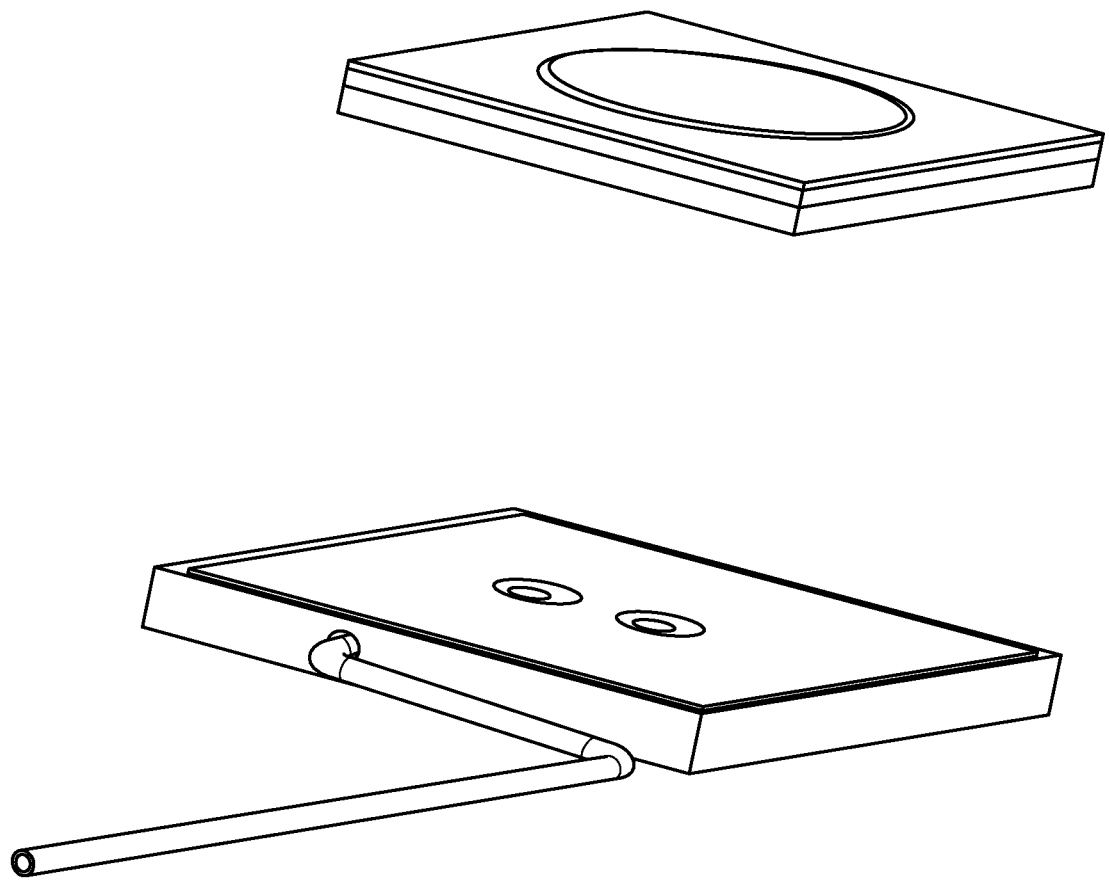
FIG. 19 depicts the MEMS pump assembly and the titanium manifold of FIG. 18 with their respective preparatory surfaces attached.
Figure 20:
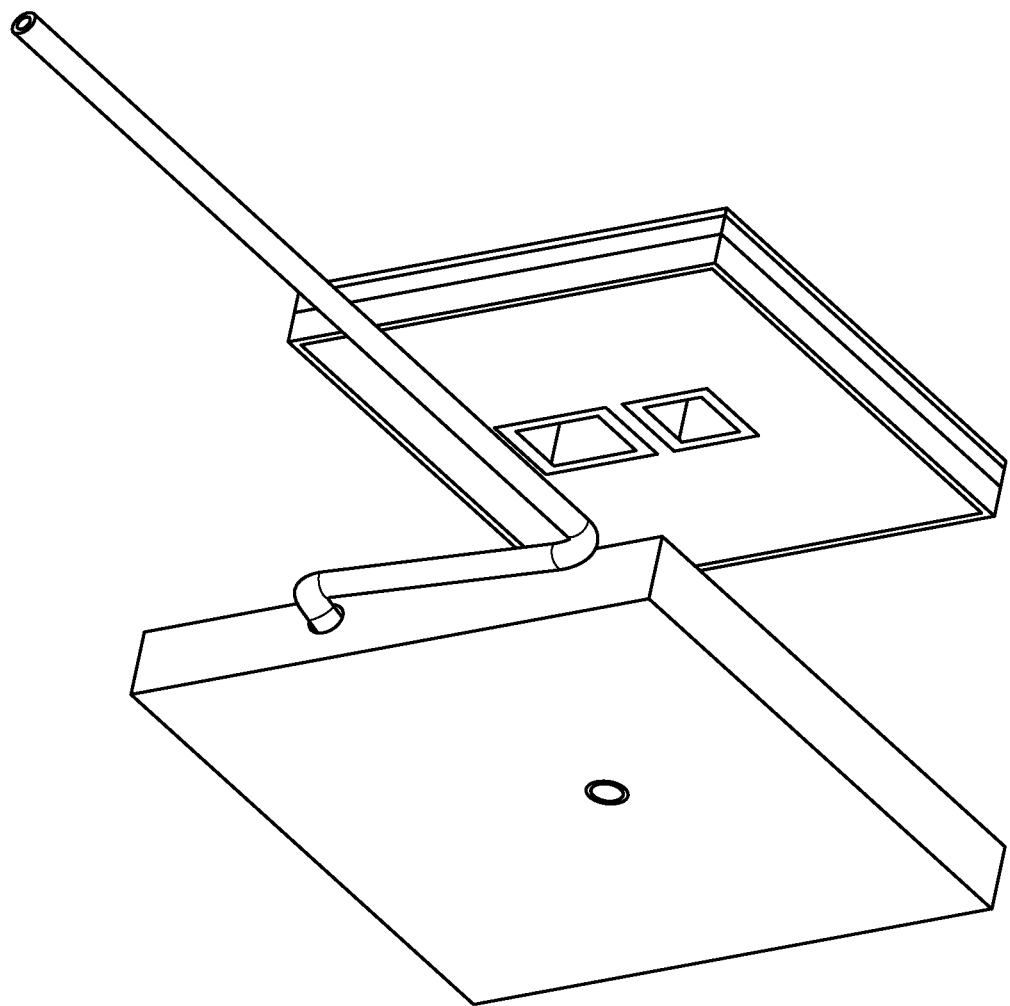
FIG. 20 depicts the MEMS pump assembly and the titanium manifold of FIG. 19 from a different perspective view.

FIGS. 18-26 depict alternate examples of attaching a MEMS pump to a titanium manifold, according to an exemplary embodiment of the present invention. With reference to FIG. 18, an exemplary MEMS pump assembly is shown on top and an exemplary titanium manifold is shown on the bottom of the figure, each with a layer to be attached to the top and bottom surfaces to be joined. FIG. 18 thus illustrates essentially the same process as described above, but without the gasket. In this embodiment, it is noted, the fluid seal between inlet and outlet is not accessible for testing. In such embodiments, a reliable enough seal between inlet and outlet may be obtained without the use of a double O-ring, which makes for a more cost-effective design. Here the indium layer is plated on the underside of the silicon pump, and brazed to the manifold, which has been prepared as described above, ultimately with a gold plating on top. FIGS. 19 and 20 depict the same process as is shown in FIG. 18, from different views.

Figure 21:
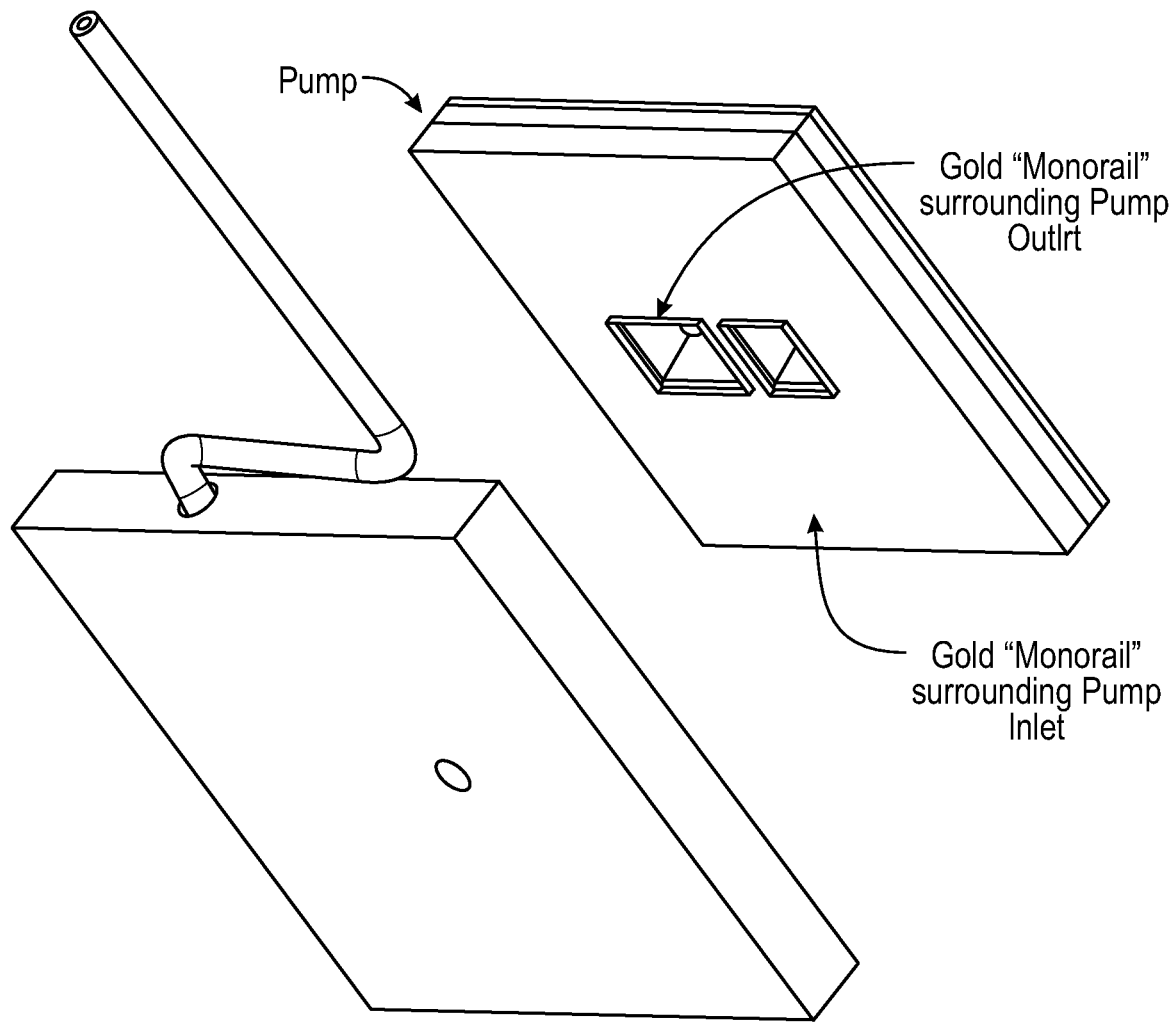
FIG. 21 depicts an alternate gasket-less embodiment, where the MEMS pump is provided with a gold "monorail" surrounding each of the inlet and outlet of the pump.
Figure 22:
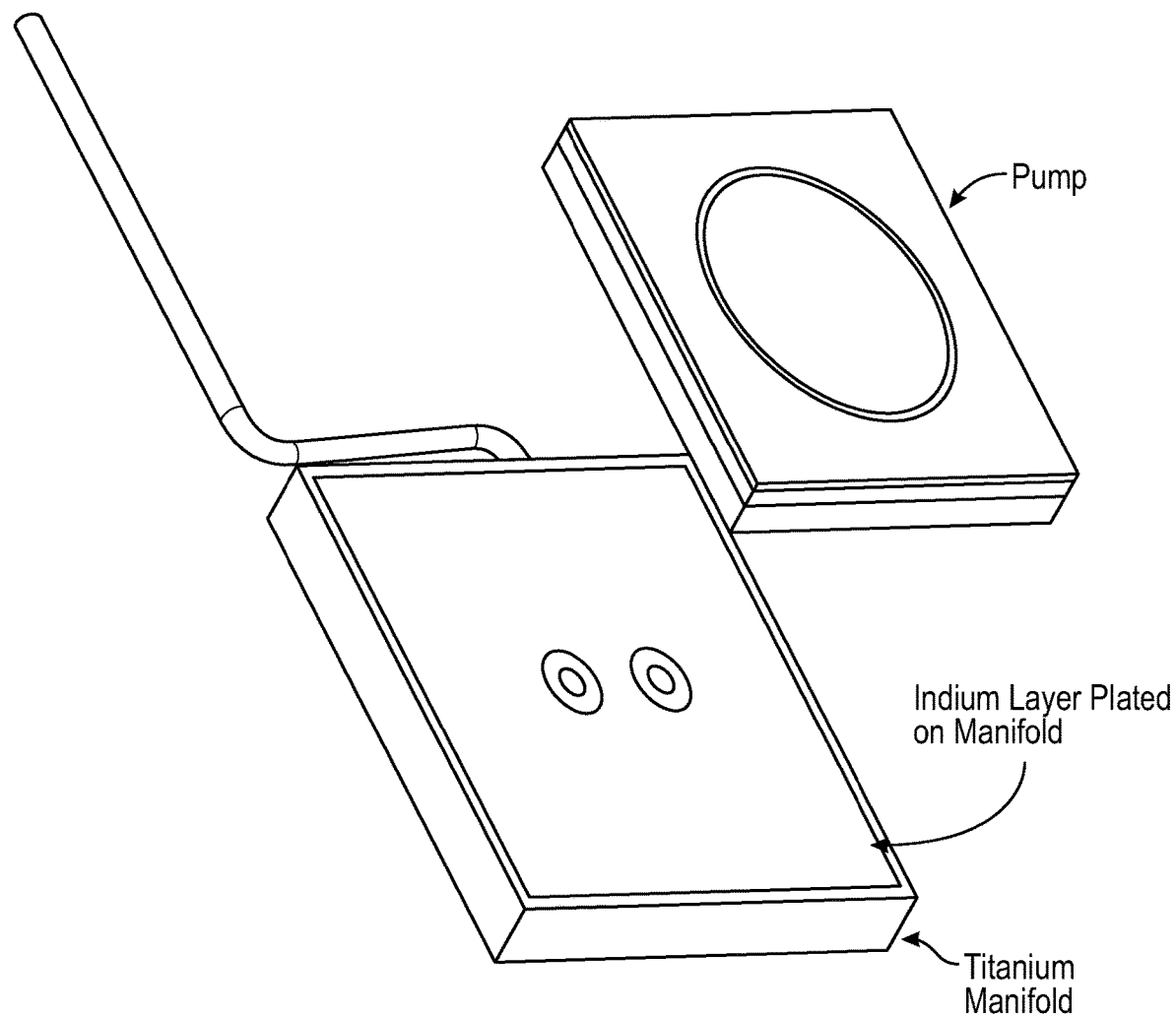
FIG. 22 illustrates the MEMS pump assembly and the titanium manifold as seen in FIG. 21 from a different perspective, showing the upper surface of the manifold with an indium plate layer on its top surface.

FIGS. 21-22 present another gasketless configuration using an indium-silver soldering joint, a gold thermo-compression bond, or a glass seal. In FIG. 21 a gold "monorail" on the pump bottom, surrounding the pump inlet and outlet, is brazed to a gold plated layer on the titanium manifold. In FIG. 22 an indium layer plated on the manifold is brazed to the bottom surface of the pump assembly.

Figure 23:
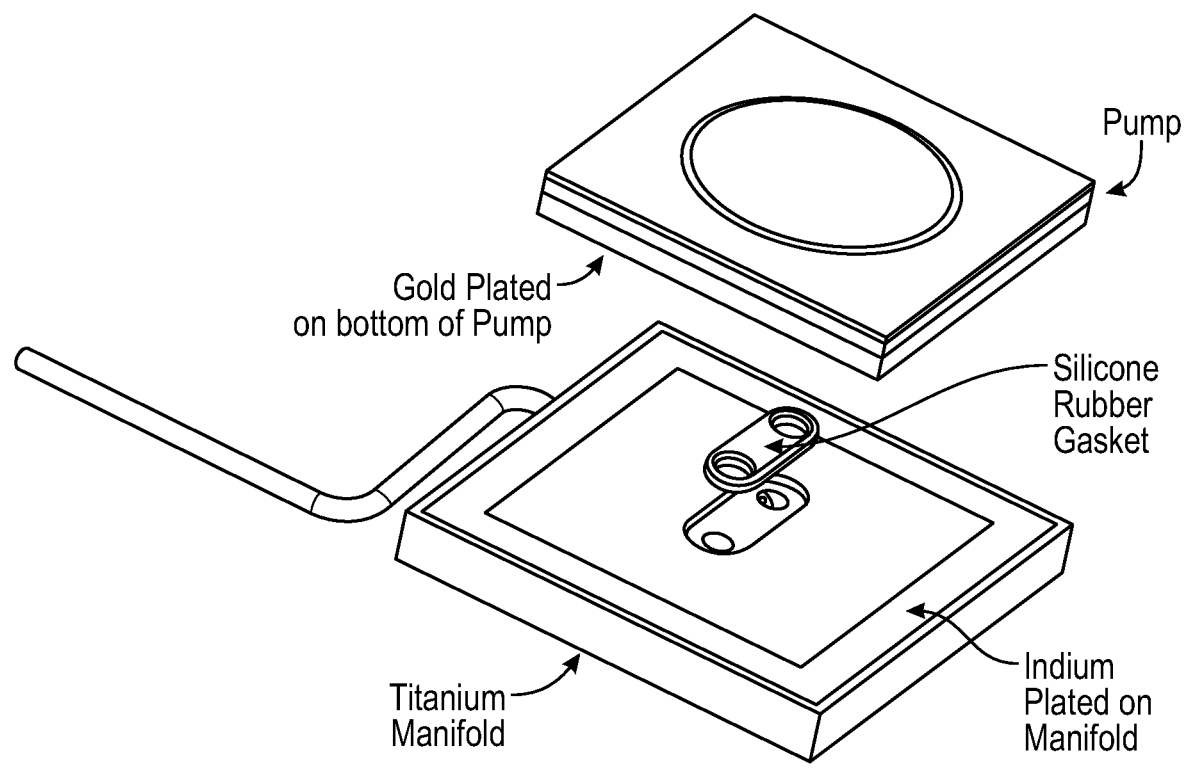
FIGS. 23 and 24 illustrate a similar process as that described in connection with FIGS. 1-17, using silicone rubber gaskets to seal around the pump inlet and outlet, and the pump assembly, now having been gold plated on its bottom surface, ready to be attached to the upper surface of the titanium manifold, which itself has been plated with indium.
Figure 24:
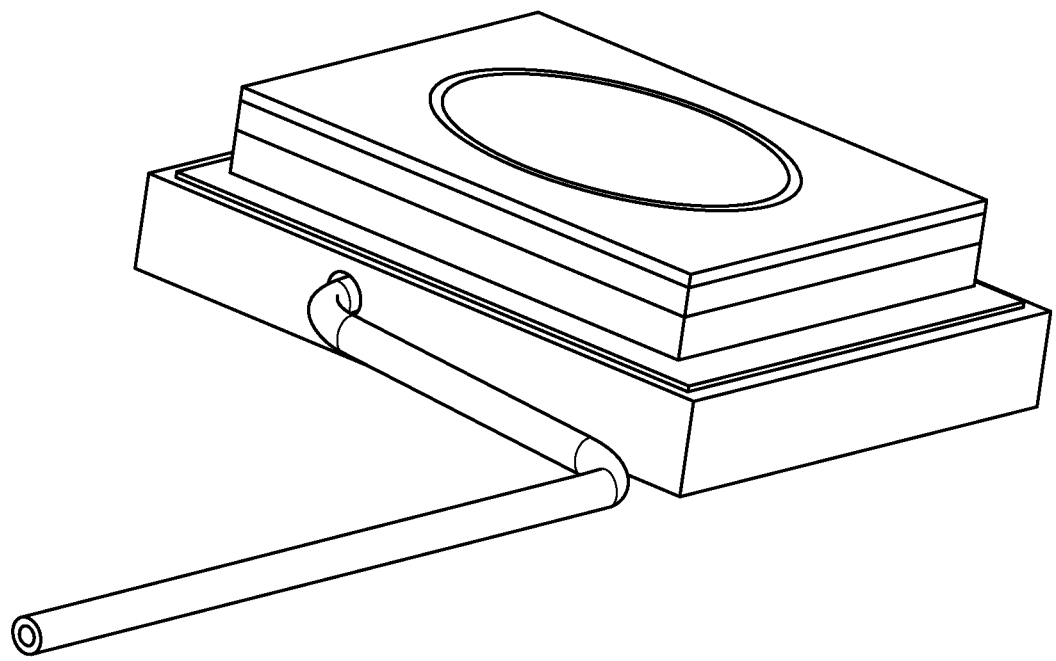

FIGS. 23 and 24 depict a similar process as the one shown in FIGS. 1-17, and described above with reference to those figures, except in place of two O-rings a silicone rubber gasket is used to doubly seal the inlet from the outlet. An indium frame plated onto the top of the manifold is brazed to a gold plate layer on the underside of a pump assembly. Thus, the silicone gasket seals around the pump inlet and outlet, and a braze holds the pump to the manifold, as shown.

Figure 25:
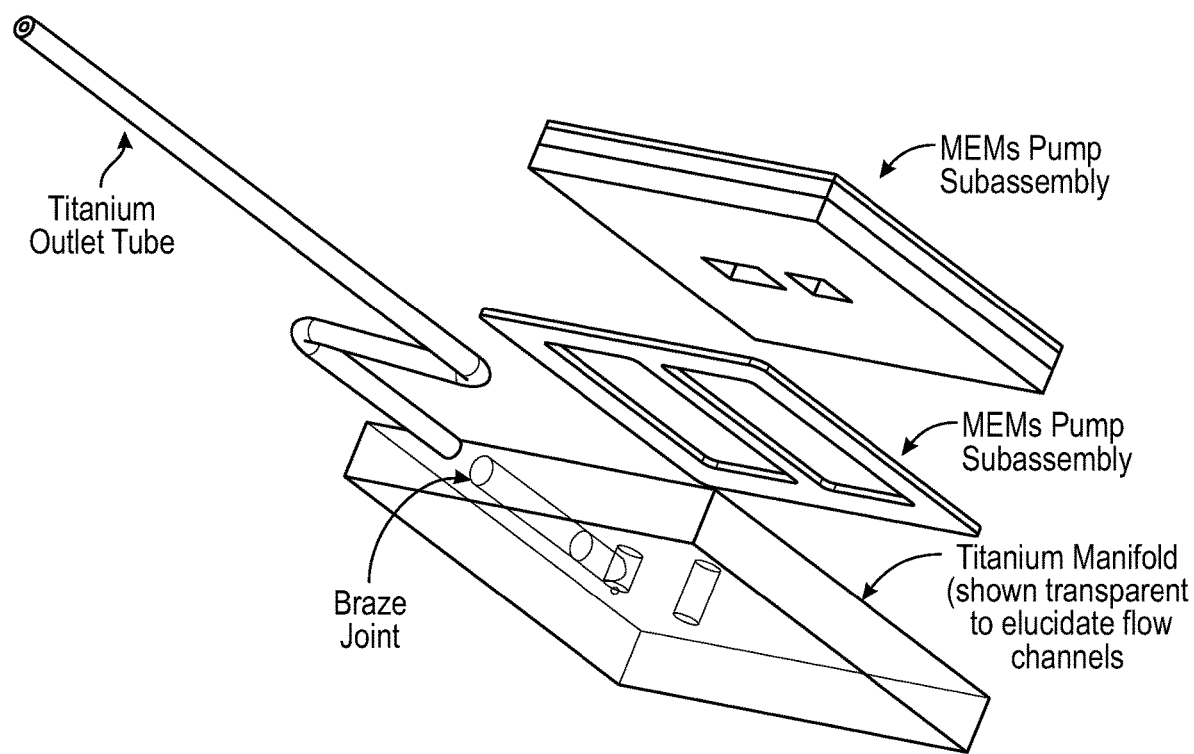
FIG. 25 depicts another alternate process for joining a MEMS pump to a titanium manifold, using a glass frit preform; an exploded view of the two subassemblies (MEMS pump and titanium manifold) is depicted, prior to joining.
Figure 26:
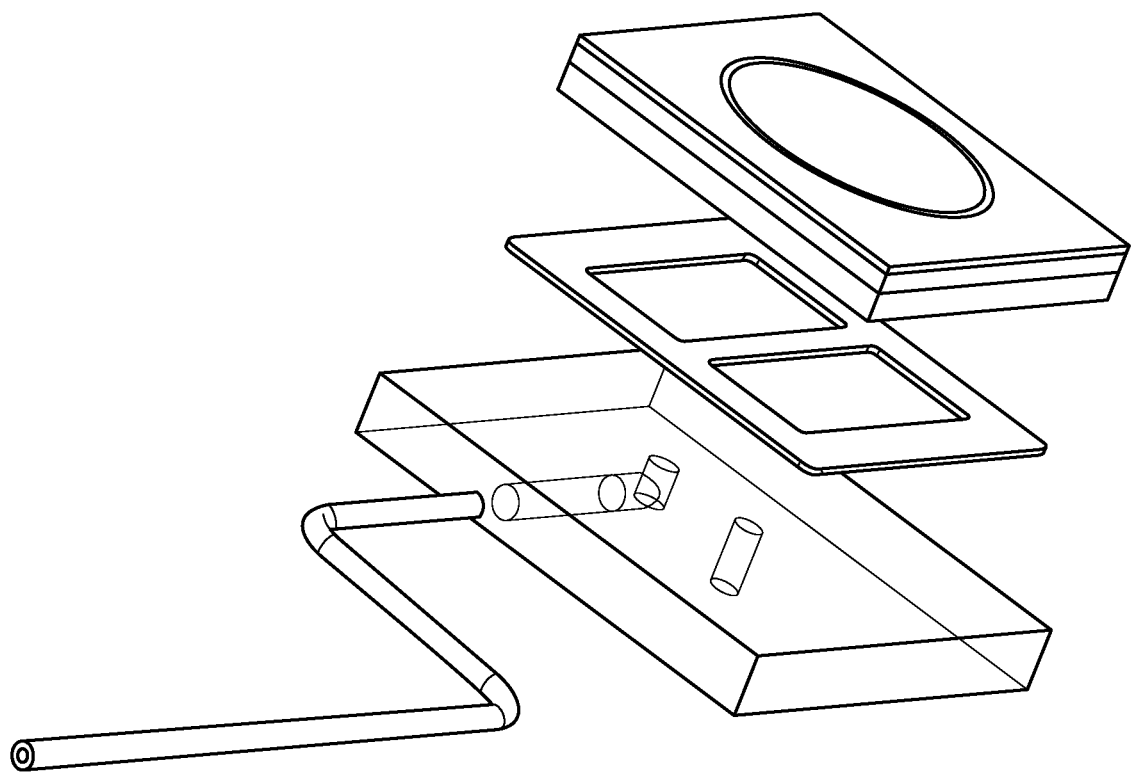
FIG. 26 depicts the same exploded view of FIG. 25 from a different perspective.

FIGS. 25 and 26 illustrate yet an alternate process wherein all of the solder joints are replaced with a glass seal or a gold thermo-compression bond. It is noted, however, that the CTE and greater temperature excursions needed for a glass joint, as well as the limited ability of these materials to accommodate strain, make thermo-compression bonding and glass seals somewhat less desirable. Further, because the temperatures for these processes also exceed the Curie point of the piezo actuator as well as the epoxy that holds it in place, in these embodiments the processing steps may be reordered to create the manifold-MEMS pump joint first. Thus, in such embodiments, the glass frit, or thermo-compression bonding, would be done before the piezoelectric actuator is epoxied to the silicon MEMS pump; otherwise the frit and thermo-compression bonding temperatures would damage both the piezo and the epoxy. This can add complexity and cost in such embodiments.

As shown in FIGS. 25 and 26, in embodiments, a glass seal could be used 1:1 in place of the braze described above with a different surface preparation. In embodiments, to prepare a surface for glass sealing, the joint would need to be a trough design to avoid CTE cracking.

Finally, it is noted that thermos-compression bonding is possible with a thickness similar to the indium thickness gold layer and a gold projection from one of the surfaces.

However Au—Au bonding requires a temperature of 300° C. This is well above the Curie Point for the peizo actuator and the softening point for the epoxy.

Example Silicon and Metal Surface Preparatory Processes

The following presents two example processes for preparing pumps and manifolds for soldering, according to embodiments of the present invention. In embodiments, the techniques may be used for any silicon and metallic surfaces that are desired to be soldered together. The first example describes a Ni/TiW/Au process for micro-pump chips, and the second a TiW/Ni/Au process for micro-pump chips. Each of the two micro-pump chip processes is followed by a protocol for preparing a titanium manifold (the same in each example). These exemplary processes may, in embodiments, be used in the assembly of a microfluidic device, such as is illustrated in FIGS. 1 and 2, described above.

A. Pump and Manifold Solder Metalization Process for Ni/TiW/Au on Micro-Pump Chips:
1. Have blue-tape pieces pre-cut and ready
2. Take pump off of gel-pak and place under stereoscope on soft towel or gelpak
3. Under scope, use tweezers to place tape as close as possible to desired position
4. Make sure tape is pressed uniformly on surface (this will prevent liquid surface treatment chemical from getting under the tape and into the pump orifices)
5. Go to HF acid bench and prepare large dish with DI water for rinse.
6. Using a polyethylene pipette, place enough BHF (Buffered HF, 8% HF) to coat masked surface with a bead of acid.
7. Wait until acid recedes from silicon surface and forms a bead on the tape.
8. Place in the DI water to rinse. Rinse for 15 seconds. Dry with N2 gun, both sides.
9. Place samples with piezo-side down onto blue tape and cut around edges (this blue tape will make it easy to remove from the carrier when sputtering is done)
10. Use a small piece of 2-sided Kapton tape on a carrier wafer for each pump.
11. Place each pump unit on the 2-sided tape and make sure parts are stably attached.
12. Load into AJA sputtering system.
13. Prior to sputtering on sample, condition Ni, TiW, Au targets for 3 minutes under normal operation with shutter closed.
14. Conditions and rates for materials
    a. AJA sputter 3, 44 on height, 4 on gun tilt.
    b. Ni: 25 sccm Ar, 3 mT, 200 W, 9.4 nm/min
    c. TiW: 25 sccm Ar, 4.5 mT, 300 W, 10 nm/min (make sure voltage in compliance and stable)
    d. Au: 25 sccm Ar, 10 mT, 300 W, 45 nm/min
15. Sputter using time to following thicknesses
    a. TiW: 50 nm
    b. Ni: 250 nm
    c. Au: 1000 nm
16. Remove samples from sputter system
17. Using proper tweezers (small tip with jagged grip ends), under stereoscope, carefully remove protective tape from pump part. Metal may flake a little at the corner while first grabbing tape.
18. Lift pump off of carrier and remove blue tape from piezo-side of pump.
19. Place face down in a new, clean gelpak to keep pump orifices clean of particulates.

Process for Ti-Manifolds:
1. Have manifold-tape pieces pre-cut and ready
2. Take manifold out of package
3. Go to acid bench and prepare large dish with DI water for rinse.
4. Mix NH4OH (30% concentration):DI Water 1:2 in a small beaker.
5. Hold sample upside down with tweezers so that surface is in base.
6. Let sit for 30 s.
7. Place in the DI water to rinse. Rinse for 30 seconds. Dry with N2 gun, both sides. Make sure to dry holes thoroughly.

8. Under scope, use tweezers to place tape as close as possible to desired position
9. Make sure tape is pressed uniformly on surface
10. Use small piece of blue tape to protect side hole (larger one with smaller hole in center)
11. Place samples with non-protected-side down onto blue tape and cut around edges (leave 2 sides of tape exposed for mounting to carrier wafer)
12. Use Kapton tape to hold manifolds on carrier by taping over the exposed blue tape.
13. Load into AJA sputtering system.
14. Prior to sputtering on sample, condition Ni, Au targets for 3 minutes under normal operation with shutter closed.
15. Conditions and rates for materials
   a. AJA sputter 3, 44 on height, 4 on gun tilt.
   b. Ni: 25 sccm Ar, 3 mT, 200 W, 9.4 nm/min
   c. Au: 25 sccm Ar, 10 mT, 300 W, 45 nm/min
16. Sputter using time to following thicknesses
   a. Ni: 2 minutes for about 20 nm
   b. Au: 22 minutes for about 1000 nm
17. Remove samples from sputter system
18. Using proper tweezers (small tip with jagged grip ends), under stereoscope, carefully remove protective tape from pump part. Metal may flake a little at the corner while first grabbing tape.
19. Cut manifold off of carrier. Leave blue tape on bottom to protect from particles.
20. Place face down in a new, clean gelpak to keep orifices clean of particulates.

B. Process for TiW/Ni/Au on Micro-Pump Chips:
1. Have blue-tape pieces pre-cut and ready
2. Take pump off of gel-pak and place under stereoscope on soft towel or gelpak
3. Under scope, use tweezers to place tape as close as possible to desired position
4. Make sure tape is pressed uniformly on surface (this will prevent liquid surface treatment chemical from getting under the tape and into the pump orifices)
5. Go to HF acid bench and prepare large dish with DI water for rinse.
6. Using a polyethylene pipette, place enough BHF (Buffered HF, 8% HF) to coat masked surface with a bead of acid.
7. Wait until acid recedes from silicon surface and forms a bead on the tape.
8. Place in the DI water to rinse. Rinse for 15 seconds. Dry with N2 gun, both sides.
9. Place samples with piezo-side down onto blue tape and cut around edges (this blue tape will make it easy to remove from the carrier when sputtering is done)
10. Use a small piece of 2-sided Kapton tape on a carrier wafer for each pump.
11. Place each pump unit on the 2-sided tape and make sure parts are stably attached.
12. Load into AJA sputtering system.
13. Prior to sputtering on sample, condition Ni, TiW, Au targets for 3 minutes under normal operation with shutter closed.
14. Conditions and rates for materials
   a. AJA sputter 3, 44 on height, 4 on gun tilt.
   b. TiW: 25 sccm Ar, 4.5 mT, 300 W, 10 nm/min (make sure voltage in compliance and stable)
   c. Ni: 25 sccm Ar, 3 mT, 200 W, 9.4 nm/min
   d. Au: 25 sccm Ar, 10 mT, 300 W, 45 nm/min
15. Sputter using time to following thicknesses
   a. TiW: 50 nm
   b. Ni: 250 nm
   c. Au: 1000 nm
16. Remove samples from sputter system
17. Using proper tweezers (small tip with jagged grip ends), under stereoscope, carefully remove protective tape from pump part. Metal may flake a little at the corner while first grabbing tape.
18. Lift pump off of carrier and remove blue tape from piezo-side of pump.
19. Place face down in a new, clean gelpak to keep pump orifices clean of particulates.

Process for Ti-Manifolds:
1. Have manifold-tape pieces pre-cut and ready
2. Take manifold out of package
3. Go to acid bench and prepare large dish with DI water for rinse.
4. Mix $NH_4OH$ (30% concentration):DI Water 1:2 in a small beaker.
5. Hold sample upside down with tweezers so that surface is in base.
6. Let sit for 30 s.
7. Place in the DI water to rinse. Rinse for 30 seconds. Dry with N2 gun, both sides. Make sure to dry holes thoroughly.
8. Under scope, use tweezers to place tape as close as possible to desired position
9. Make sure tape is pressed uniformly on surface
10. Use small piece of blue tape to protect side hole (larger one with smaller hole in center)
11. Place samples with non-protected-side down onto blue tape and cut around edges (leave 2 sides of tape exposed for mounting to carrier wafer)
12. Use Kapton tape to hold manifolds on carrier by taping over the exposed blue tape.
13. Load into AJA sputtering system.
14. Prior to sputtering on sample, condition Ni, Au targets for 3 minutes under normal operation with shutter closed.
15. Conditions and rates for materials
   a. AJA sputter 3, 44 on height, 4 on gun tilt.
   b. Ni: 25 sccm Ar, 3 mT, 200 W, 9.4 nm/min
   c. Au: 25 sccm Ar, 10 mT, 300 W, 45 nm/min
16. Sputter using time to following thicknesses
   a. Ni: 2 minutes for about 20 nm
   b. Au: 22 minutes for about 1000 nm
17. Remove samples from sputter system
18. Using proper tweezers (small tip with jagged grip ends), under stereoscope, carefully remove protective tape from pump part. Metal may flake a little at the corner while first grabbing tape.
19. Cut manifold off of carrier. Leave blue tape on bottom to protect from particles.
20. Place face down in a new, clean gelpak to keep orifices clean of particulates.

Illustrative examples of the technologies disclosed herein are provided below. An embodiment of the technologies may include any one or more, and any combination of, the examples described below.

What is claimed:
1. A microfluidic device, comprising:
a silicon device including a first solderable surface;
a metallic component including a second solderable surface; and
a solder joint attaching the first solderable surface to the second solderable surface, the solder joint comprising a homogenous single composition solder and having a pre-defined thickness configured to accommodate strain due to co-efficient of thermal expansion (CTE) mismatch between the silicon device and the metallic component without breaking apart,
wherein the homogenous single composition solder is a silver-indium solder comprising 97% indium by weight, the pre-defined thickness is greater than or equal to 25 µm, and the homogeneous single composition solder has a melting point less than or equal to 160° C.

2. The microfluidic device of claim 1, wherein at least one of:
the silicon device is a MEMS pump;
the metallic component is a titanium manifold;
the solder joint is configured to distribute overall shear strain through the solder joint;
or
the solder joint is configured to distribute overall shear strain through the solder joint and the pre-defined thickness is such that the strain of the solder joint does not exceed the shear strength of the solder.

3. The microfluidic device of claim 1, wherein the silicon device is a MEMS pump, the metallic component is a titanium manifold, and wherein:
the first solderable surface is prepared by:
removing a silicon oxide coating;
sputtering the first solderable surface with an adhesion promoter;
depositing a layer of nickel; and
depositing a layer of gold onto the layer of nickel.

4. The microfluidic device of claim 1, wherein the silicon device is a MEMS pump, the metallic component is a titanium manifold, and wherein:
the second solderable surface is prepared by:
grinding the second solderable surface flat;
plating electroless nickel onto the surface to form an electroless nickel plated surface;
heating the electroless nickel plated surface to a temperature where any metallic oxide breaks down and the nickel alloys with the second solderable surface; and
coating the electroless nickel plated surface with gold.

5. A method of fabricating the microfluidic device of claim 1, comprising:
preparing the first solderable surface for soldering;
preparing the second solderable for soldering; and
soldering the first surface to the second surface using the solder joint.

6. The method of fabricating of claim 5, wherein at least one of:
the silicon device is a MEMS pump, the metallic component is a titanium manifold, and the MEMS pump and the titanium manifold are provided in a microfluidic device;
the solder is deposited between the first and second solderable surfaces in the pre-defined thickness to distribute overall shear strain through the solder joint;
or
the solder is deposited between the first and second solderable surfaces in the pre-defined thickness to distribute overall shear strain through the solder joint, and the pre-defined thickness is such that the strain of the solder joint does not exceed the shear strength of the solder.

7. The method of fabricating of claim 5, wherein the silicon device is a MEMS pump having an upper surface and a lower surface, the metallic component is a titanium manifold, the lower surface of the MEMS pump is prepared by:
removing a silicon oxide coating;
sputtering the lower surface with an adhesion promoter;
depositing a layer of nickel; and
depositing a layer of gold onto the layer of nickel.

8. The method of fabricating of claim 7, wherein at least one of:
the silicon oxide coating is removed by buffered hydrofluoric acid;
the adhesion promoter is titanium tungsten;
or
the lower surface is prepared by:
sputtering the lower surface with a metallic silicide;
depositing a layer of nickel; and
depositing a layer of gold onto the layer of nickel.

9. The method of fabricating of claim 5, wherein the silicon device has a lower surface, the lower surface is the first solderable surface, and wherein the lower surface is prepared by either:
removing a silicon oxide coating with an acid wash;
depositing a layer of nickel; and
depositing a layer of gold onto the layer of nickel,
or
removing a silicon oxide coating with buffered hydrofluoric acid;
depositing a layer of nickel; and
depositing a layer of gold onto the layer of nickel.

10. The method of fabricating of claim 5, wherein at least one of:
the metallic component has an upper surface, the upper surface is the second solderable surface, and the upper surface is prepared by:
grinding the upper surface flat;
plating electroless nickel onto the upper surface to form an electroless nickel plated surface;
heating the electroless nickel plated surface to a temperature where any metallic oxide breaks down and the nickel of the electroless nickel plated surface alloys with the upper surface; and
coating the electroless nickel plated surface with gold,
or
the metallic component is a titanium manifold having an upper surface, the upper surface is the second solderable surface, and the upper surface is prepared by:
grinding the upper surface flat with a 1000 grit finish;
plating electroless nickel onto the upper surface to form an electroless nickel plated surface;
heating the electroless nickel plated surface to a temperature where any metallic oxide breaks down and the nickel of the electroless nickel plated surface alloys with the upper surface; and
coating the electroless nickel plated surface with gold.

11. The method of fabricating of claim 10, wherein:
the electroless nickel plated surface is heated to between 375 and 425° C. for between 30 and 60 minutes; or
the electroless nickel plated surface is heated for a time such that any titanium oxide in the titanium manifold breaks down and the nickel of the electroless nickel plated surface alloys with the titanium of the titanium manifold, to create in a transition zone on the top of the titanium manifold comprising a transition from titanium to nickel titanium alloy to a pure nickel surface.

12. The method of fabricating of claim 5, wherein at least one of:
the homogenous single composition solder comprises 97% Indium and 3% silver by weight; or
the soldering is controlled to occur at a temperature between 140° C. and 160° C.

13. The method of fabricating of claim 5, wherein the metallic component has an upper surface, the upper surface is the second solderable surface, and the upper surface is prepared by:
grinding the upper surface flat;
plating electroless nickel onto the surface to form an electroless nickel plated surface;
heating the electroless nickel plated surface to a temperature where any metallic oxide breaks down and the nickel of the electroless nickel plated surface alloys with the upper surface; and
coating the electroless nickel plated surface with gold.

14. The method of fabricating of claim 13, wherein the metallic component is a titanium manifold, and wherein at least one of:
the upper surface of the titanium manifold is ground flat with a 1000 grit finish;
the electroless nickel plated surface is heated to between 375 and 425° C. for between 30 and 60 minutes.

15. The method of fabricating of claim 13, wherein at least one of:
coating the electroless nickel plated surface with gold further comprises cleaning the electroless nickel plated surface with an ammonia containing cleaning agent followed by sputtering the electroless nickel plated surface with another layer of nickel, followed by a layer of gold;
the solder is an indium silver solder, comprising 97% Indium and 3% silver by weight;
or
the soldering is controlled to occur at a temperature between 140° C. and 160° C.

16. The method of fabrication of claim 10, wherein coating the electroless nickel plated surface with gold includes cleaning the electroless nickel plated surface with an ammonia containing cleaning agent followed by sputtering the electroless nickel plated surface with another layer of nickel, followed by a layer of gold.

17. The method of fabrication of claim 13, wherein the electroless nickel plated surface is heated to a temperature and for a time such that any titanium oxide in the titanium manifold breaks down and the nickel of the electroless nickel plated surface alloys with the titanium in the titanium manifold, thereby resulting in a transition zone on the top of the titanium manifold comprising a transition from titanium to nickel titanium alloy to a pure nickel surface.

18. A microfluidic device, comprising:
a silicon device including a first solderable surface;
a metallic component including a second solderable surface; and
a solder joint connected to the first solderable surface and to the second solderable surface, the solder joint comprising a homogenous single composition solder and having a pre-defined thickness configured to accommodate strain due to co-efficient of thermal expansion (CTE) mismatch between the silicon device and the metallic component,
wherein the homogenous single composition solder is an indium silver solder, the pre-defined thickness is greater than or equal to 25 µm, and the solidus point of the solder is less than or equal to 160° C.

19. The microfluidic device of claim 18, wherein the homogenous single composition solder comprises 97% indium by weight.

20. The microfluidic device of claim 18, wherein the solder joint is one of: a fillet joint or a trough joint.

* * * * *